US010895582B2

(12) United States Patent
Buschke

(10) Patent No.: US 10,895,582 B2
(45) Date of Patent: Jan. 19, 2021

(54) SAMPLE PREPARING APPARATUS, SAMPLE PREPARING SYSTEM, SAMPLE PREPARING METHOD, AND PARTICLE ANALYZER

(71) Applicant: SYSMEX CORPORATION, Kobe (JP)

(72) Inventor: David Buschke, Franklin, WI (US)

(73) Assignee: SYSMEX CORPORATION, Kobe (JP)

(*) Notice: Subject to any disclaimer, the term of this patent is extended or adjusted under 35 U.S.C. 154(b) by 397 days.

(21) Appl. No.: 15/697,994

(22) Filed: Sep. 7, 2017

(65) Prior Publication Data

US 2019/0072578 A1 Mar. 7, 2019

(51) Int. Cl.

| | |
|---|---|
| ***G01N 35/08*** | (2006.01) |
| ***G01N 35/10*** | (2006.01) |
| ***G01N 1/31*** | (2006.01) |
| ***G01N 33/49*** | (2006.01) |
| ***G01N 11/00*** | (2006.01) |

(Continued)

(52) U.S. Cl.

CPC ........... *G01N 35/1009* (2013.01); *G01N 1/14* (2013.01); *G01N 1/31* (2013.01); *G01N 1/38* (2013.01); *G01N 1/4077* (2013.01); *G01N 11/00* (2013.01); *G01N 15/1404* (2013.01); *G01N 15/1459* (2013.01); *G01N 33/49* (2013.01); *G01N 35/1016* (2013.01); *G01N 35/1095* (2013.01); *G01N 2001/1418* (2013.01); *G01N 2001/4083* (2013.01); *G01N 2011/006* (2013.01);

(Continued)

(58) Field of Classification Search

CPC . G01N 2035/00524; G01N 2015/0092; G01N 33/86

USPC .................................................. 700/285, 283

See application file for complete search history.

(56) References Cited

U.S. PATENT DOCUMENTS

2004/0190367 A1* 9/2004 Wierzbicki ....... B01F 15/00207 366/140

2011/0014646 A1 1/2011 Fukuda et al.

FOREIGN PATENT DOCUMENTS

EP 2487491 A1 8/2012

JP H04-151541 A 5/1992

(Continued)

OTHER PUBLICATIONS

Extended European Search Report for Europe Appln 18192424.2, dated Jan. 29, 2019, 12 pages.

*Primary Examiner* — Natalia Levkovich

(74) *Attorney, Agent, or Firm* — Brinks Gilson & Lione

(57) ABSTRACT

To accurately analyze measurement target particles in each specimen, while reducing variation in dispensing amounts of specimens which is caused by different viscosities of the respective specimens. A sample preparing apparatus 1 includes: a measurement section 2 configured to measure a specimen obtained from a specimen container 10, and obtain viscosity information relating to viscosity of the specimen; a sample preparation section 3 configured to prepare a measurement sample by aspirating the specimen from the specimen container 10, discharging the specimen into a mixing container 11, and mixing the specimen with a labeling substance in the mixing container 11; and a control section 4 configured to determine, on the basis of viscosity information, at least one of an aspiration condition for aspirating the specimen and a discharge condition for discharging the specimen, and control the sample preparation section 3.

22 Claims, 30 Drawing Sheets

(51) Int. Cl.

| | |
|---|---|
| ***G01N 15/14*** | (2006.01) |
| ***G01N 1/14*** | (2006.01) |
| ***G01N 1/38*** | (2006.01) |
| ***G01N 1/40*** | (2006.01) |
| *G01N 15/10* | (2006.01) |
| *G01N 35/00* | (2006.01) |

(52) U.S. Cl.
CPC ................ *G01N 2015/1006* (2013.01); *G01N 2035/00495* (2013.01); *G01N 2035/1025* (2013.01)

(56) References Cited

FOREIGN PATENT DOCUMENTS

| | | | |
|---|---|---|---|
| JP | H07-301586 | A | 11/1995 |
| JP | 2003-083851 | A | 3/2003 |
| JP | 2008-224386 | A | 9/2008 |

* cited by examiner

FIG. 13A

| ID OF TEST ITEM | NAME OF TEST ITEM | ID OF CELL DETECTION REAGENT | NAME OF CELL DETECTION REAGENT | MEASUREMENT ITEM | TYPE OF FLUORESCENT SUBSTANCE | TYPE OF SPECIMEN | NUMBER OF WHITE BLOOD CELLS NECESSARY FOR TEST ITEM | PERCENTAGE OF MEASUREMENT TARGET CELLS | AMOUNT OF SPECIMEN | MIXING AMOUNT OF CELL DETECTION REAGENT WITH RESPECT TO AMOUNT OF SPECIMEN | ORDER OF ADDING CELL DETECTION REAGENTS | NECESSARY NUMBER OF WHITE BLOOD CELLS FOR EACH CELL DETECTION REAGENT |
|---|---|---|---|---|---|---|---|---|---|---|---|---|
| A | REGULATORY T CELL | 1 | NUCLEUS STAIN LIQUID | NUCLEUS | Hoechst 33342 | PERIPHERAL BLOOD | 10000 | ABOUT 10% OF ALL WHITE BLOOD CELLS IN PERIPHERAL BLOOD | 10 μl | 5 μl | HEMOLYZING AGENT (5 μl) ↓ CELL DETECTION REAGENT 2 ↓ CELL DETECTION REAGENT 3 ↓ CELL MEMBRANE PERMEABLE AGENT (10 μl) ↓ CELL DETECTION REAGENT 4 ↓ CELL DETECTION REAGENT 1 | 1000 |
| | | 2 | CD25 | CD25 | PE | | | | | 10 μl | | 5000 |
| | | 3 | T CELL SURFACE MARKER COCKTAIL ANTIBODY REAGENT | CD3 | FITC | | | | | 5 μl | | 1000 |
| | | | | CD4 | PC7 | | | | | | | |
| | | 4 | FoxP3 | FoxP3 | Alexa 647 | | | | | 10 μl | | 10000 |

FIG. 13B

| ID OF TEST ITEM | NAME OF TEST ITEM | MEASUREMENT SAMPLE NO. | ID OF CELL DETECTION REAGENT | NAME OF CELL DETECTION REAGENT | MEASUREMENT ITEM | TYPE OF FLUORESCENT SUBSTANCE | TYPE OF SPECIMEN | NECESSARY NUMBER OF WHITE BLOOD CELLS FOR EACH CELL DETECTION REAGENT | PERCENTAGE OF MEASUREMENT TARGET CELLS TO ALL WHITE BLOOD CELLS OF PERIPHERAL BLOOD | AMOUNT OF SPECIMEN | MIXING AMOUNT OF CELL DETECTION REAGENT WITH RESPECT TO AMOUNT OF SPECIMEN | TYPE AND DISPENSING AMOUNT OF REAGENT OTHER THAN CELL DETECTION REAGENT | PRIORITY ORDER WHEN NUMBER OF CELLS IS INSUFFICIENT |
|---|---|---|---|---|---|---|---|---|---|---|---|---|---|
| A | REGULATORY T CELL | 1 | 1 | NUCLEUS STAIN LIQUID | NUCLEUS | Hoechst 33342 | PERIPHERAL BLOOD | 1000 | 20% | 10 μl | 5 μl | HEMOLYZING AGENT 5 μl | 2 |
| | | | 2 | CD25 | CD25 | PE | | 5000 | | | 10 μl | | |
| | | 2 | 1 | NUCLEUS STAIN LIQUID | NUCLEUS | Hoechst 33342 | | 1000 | 30% | | 5 μl | HEMOLYZING AGENT 5 μl | 4 |
| | | | 3 | CD3 | CD3 | FITC | | 1000 | | | 5 μl | | |
| | | 3 | 1 | NUCLEUS STAIN LIQUID | NUCLEUS | Hoechst 33342 | | 1000 | 30% | | 5 μl | HEMOLYZING AGENT 5 μl | 3 |
| | | | 4 | CD4 | CD4 | PC7 | | 1000 | | | 5 μl | | |
| | | 4 | 1 | NUCLEUS STAIN LIQUID | NUCLEUS | Hoechst 33342 | | 1000 | 10% | | 5 μl | HEMOLYZING AGENT 5 μl | 1 |
| | | | 5 | FoxP3 | FoxP3 | Alexa 647 | | 10000 | | | 10 μl | CELL MEMBRANE PERMEABLE AGENT 10 μl | |

PREPARATION OF MEASUREMENT SAMPLE FOR SPECIMEN A

DILUTION AND PREPARATION OF MEASUREMENT SAMPLE FOR SPECIMEN B

CONDENSATION AND PREPARATION OF MEASUREMENT SAMPLE FOR SPECIMEN C

FIG. 20

| HCT VALUE | Aspiration Speed μl/s | Delay ms | Excess Volume μl | Airgap μl | Dispense Speed μl/s | Breakoff Speed μl/s |
|---|---|---|---|---|---|---|
| LOW VISCOSITY <40% | 100 | 500 | 0 | STAG:0<br>LAG:10<br>TAG:6 | 450 | 400 |
| INTERMEDIATE VISCOSITY 40% - 45% | 100 | 500 | 0 | STAG:0<br>LAG:20<br>TAG:6 | 500 | 450 |
| HIGH VISCOSITY >45% | 100 | 500 | 0 | STAG:0<br>LAG:30<br>TAG:6 | 550 | 500 |

FIG. 21A

| HCT VALUE | Aspiration Speed μl/s | Delay ms | Excess Volume μl | Airgap μl | Dispense Speed μl/s | Breakoff Speed μl/s |
|---|---|---|---|---|---|---|
| LOW VISCOSITY <40% | 50 | 300 | 5 | STAG : 0<br>LAG : 0<br>TAG : 6 | 45 | 40 |
| INTERMEDIATE VISCOSITY 40% - 45% | 50 | 300 | 10 | STAG : 0<br>LAG : 0<br>TAG : 6 | 50 | 45 |
| HIGH VISCOSITY >45% | 50 | 300 | 15 | STAG : 0<br>LAG : 0<br>TAG : 6 | 55 | 50 |

FIG. 21B

| HCT VALUE | Aspiration Speed μl/s | Delay ms | Excess Volume μl | Airgap μl | Dispense Speed μl/s | Breakoff Speed μl/s |
|---|---|---|---|---|---|---|
| LOW VISCOSITY <40% | 300 | 500 | 20 | STAG : 0<br>LAG : 0<br>TAG : 6 | 450 | 400 |
| INTERMEDIATE VISCOSITY 40% - 45% | 300 | 500 | 30 | STAG : 0<br>LAG : 0<br>TAG : 6 | 500 | 450 |
| HIGH VISCOSITY >45% | 300 | 500 | 40 | STAG : 0<br>LAG : 0<br>TAG : 6 | 550 | 500 |

FIG. 21C

| HCT VALUE | Aspiration Speed µl/s | Delay ms | Excess Volume µl | Airgap µl | Dispense Speed µl/s | Breakoff Speed µl/s |
|---|---|---|---|---|---|---|
| LOW VISCOSITY <40% | 500 | 900 | 70 | STAG : 0<br>LAG : 0<br>TAG : 6 | 450 | 400 |
| INTERMEDIATE VISCOSITY 40% - 45% | 500 | 900 | 90 | STAG : 0<br>LAG : 0<br>TAG : 6 | 500 | 450 |
| HIGH VISCOSITY >45% | 500 | 900 | 110 | STAG : 0<br>LAG : 0<br>TAG : 6 | 550 | 500 |

SAMPLE PREPARING APPARATUS, SAMPLE PREPARING SYSTEM, SAMPLE PREPARING METHOD, AND PARTICLE ANALYZER

FIELD OF THE INVENTION

The present invention relates to a sample preparing apparatus, a sample preparing system, a sample preparing method, and a particle analyzer.

BACKGROUND

Patent Literature 1 discloses a sample processing apparatus including: concentration measuring means for measuring the concentration of particle components contained in a liquid sample; and a concentration unit for concentrating the sample by using the filtration function of a filter. Meanwhile, Patent Literature 2 discloses a sample preparing apparatus configured to, when detecting cancerous cells from among epidermal cells contained in an organism-derived specimen, generate concentration information reflecting the concentration of the epidermal cells contained in the organism-derived specimen, and control the amount of the organism-derived specimen to be supplied to a sample preparation section, on the basis of the concentration information.

The sample processing apparatus disclosed in Patent Literature 1 proposes to concentrate cells in a sample for the purpose of improving reproducibility (probable error) of measurement results, in a case where the concentration of particles is low in a particle analyzer such as a flow cytometer. Meanwhile, the sample preparing apparatus disclosed in Patent Literature 2 proposes to adjust the amount of the organism-derived specimen to be mixed with a stain liquid, on the basis of the concentration of the epidermal cells in the organism-derived specimen, which is obtained in pre-measurement, so that the epidermal cells are appropriately stained by the stain liquid. Further, Patent Literature 3 discloses a technique of controlling measurement conditions in a flow cytometer, on the basis of blood count data measured by the flow cytometer.

CITATION LIST

Patent Literature

[Patent Literature 1] Japanese Laid-Open Patent Publication No. H7-301586

[Patent Literature 2] International Publication WO2009/122999

[Patent Literature 3] Japanese Laid-Open Patent Publication No. H4-151541

SUMMARY OF THE INVENTION

Problems to be Solved by the Invention

Each of the sample processing apparatus disclosed in Patent Literature 1 and the sample preparing apparatus disclosed in Patent Literature 2 is based on an assumption that cell nucleuses are stained by simple stain using a dye such as ethidium bromide, acridine orange, propidium iodide, or the like, and stained cells are detected by an optical detection method.

Meanwhile, at present, in a flow cytometry test, in order to diagnose one disease, the number of types of antigens measured in response to one test request is 10 to 30 per specimen. Therefore, the mainstream of the flow cytometry test is multicolor flow cytometry in which several to ten-plus-several antigens are simultaneously measured in one analysis. In order to detect all the antigens requested to be tested, it is necessary to perform, for one specimen, multiple times of multicolor flow cytometry analysis using several types of antibodies per analysis. Further, the abundance of each of antigens existing in one cell varies depending on the antigen. In order to accurately detect a target antigen, a suitable amount of fluorescence-labeled antibody needs to be used for each antigen. In addition, regarding a stem cell such as a hematopoietic stem cell, the abundance thereof in an organism is low. Therefore, in order to assuredly detect a stem cell, the amount of the specimen to be analyzed has to be increased.

At present, determination of a mixing ratio of a specimen and a detection reagent and determination of a necessary amount of the specimen are performed on the basis of information about particle concentration in the specimen, which has been obtained by a tester in some manner. Further, preparation of measurement samples based on the determined contents is fully manually performed by the tester. Under the present situation described above, accurate flow cytometry test needs a huge amount of labor.

An object of the present invention is to efficiently perform preparation of measurement samples, and accurately analyze measurement target particles in a specimen.

Solution to the Problem

A first aspect of the present invention relates to a sample preparing apparatus 1. The sample preparing apparatus 1 according to this aspect includes: a sample preparation section 3 configured to prepare a measurement sample by dispensing a specimen from a specimen container 10 into a mixing container 11, and mixing the specimen with a reagent in the mixing container 11; and a control section 4 configured to control the sample preparation section 3 to dispense the specimen into the mixing container 11 in accordance with a dispensing condition based on a viscosity of the specimen.

A second aspect of the present invention relates to a sample preparing method. The sample preparing method according to this aspect includes steps of: dispensing a specimen from a specimen container 10 into a mixing container 11 in accordance with a condition based on a viscosity of the specimen; and preparing a measurement sample by mixing the specimen with a reagent in the mixing container 11.

A third aspect of the present invention relates to a sample preparing system 1'. The sample preparing system 1' according to this aspect includes: a sample preparing apparatus 3' configured to prepare a measurement sample by dispensing a specimen from a specimen container 10 into a mixing container 11, and mixing the specimen with a reagent in the mixing container 11; and a control device 4' connected to the sample preparing apparatus 3', and configured to control the sample preparing apparatus 3' to dispense the specimen into the mixing container 11 in accordance with a dispensing condition based on a viscosity of the specimen.

A fourth aspect of the present invention relates to a particle analyzer 100. The particle analyzer 100 according to this aspect includes: a sample preparation section 3 configured to prepare a measurement sample by dispensing a specimen from a specimen container 10 into a mixing container 11, and mixing the specimen with a reagent in the mixing container 11; a control section 4 configured to control the sample preparation section 3 to dispense the specimen into the mixing container 11 in accordance with a dispensing condition based on a viscosity of the specimen; a measurement section 2*b* configured to measure the measurement sample prepared by the sample preparation section 3 to detect measurement target particles in the measurement sample; and an analysis section 5 configured to analyze the measurement target particles on the basis of measurement data obtained by the measurement section 2*b*.

In the present invention, "dispense" means to aspirate a specimen from a specimen container and discharge the specimen into a mixing container, and a dispensing condition includes at least one of an aspiration condition for aspirating the specimen and a discharge condition for discharging the specimen.

According to the first to fourth aspects of the present invention, preparation of the measurement sample is performed by controlling, based on the viscosity of the specimen, the dispensing condition for the specimen to be dispensed when the measurement sample is prepared. Therefore, variation in dispensing amounts of specimens, which is caused by different viscosities of the respective specimens, can be reduced. Thus, the ratio of the amount of a reagent to the amount of particles contained in the specimen can be stabilized. Accordingly, measurement target particles in the specimen can be accurately analyzed.

Advantageous Effect of the Invention

According to the present invention, preparation of a measurement sample can be efficiently performed, and measurement target particles in a specimen can be accurately analyzed.

BRIEF DESCRIPTION OF THE DRAWINGS

FIG. 13A shows an example of information relating to measurement sample preparation in a case where a plurality of cell detection reagents are all dispensed into a single dispensing tube to prepare a measurement sample;

FIG. 13B shows an example of information relating to measurement sample preparation in a case where a plurality of cell detection reagents are dispensed into different dispensing tubes to prepare measurement samples;

FIG. 20 shows examples of dispensing conditions in a case where single pipetting is performed;

FIG. 21A shows conditions in a case where a set value of a dispensing amount of a specimen is 15 μl;

FIG. 21B shows conditions in a case where a set value of a dispensing amount of the specimen is 150 μl;

FIG. 21C shows conditions in a case where a set value of a dispensing amount of the specimen is 450 μl;

DETAILED DESCRIPTION OF THE PREFERRED EMBODIMENTS

Figure 1:
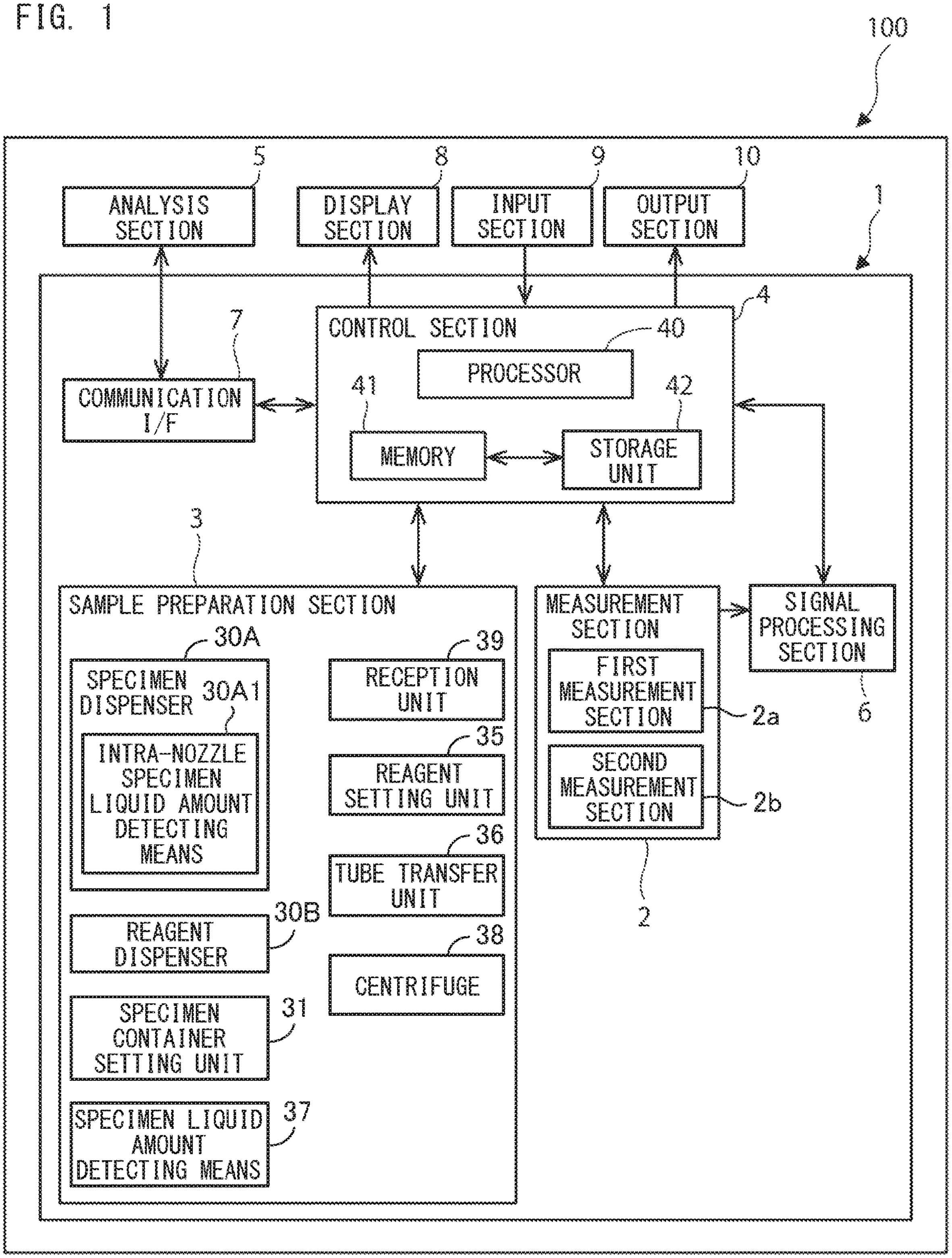
FIG. 1 is a block diagram of a sample preparing apparatus.

Hereinafter, embodiments of the present invention will be described with reference to the drawings. A sample preparing apparatus prepares a measurement sample suitable for analysis of a specimen containing particles. A particle analyzer prepares a measurement sample suitable for analysis of a specimen containing particles, and optically analyzes the prepared measurement sample, thereby performing counting of the particles contained in the specimen, or identification of the types of the particles, or both counting and identification. Specifically, for example, the sample preparing apparatus and the particle analyzer are used for detecting hematopoietic stem cells contained in cord blood and bone marrow. Further, the sample preparing apparatus and the particle analyzer are used for determining whether or not abnormal cells or the like, for example, hematopoietic tumor cells such as leukemia cells or cancer cells such as lung cancer cells, are contained in the specimen.

Particles to be measured may be, for example, artificial particles such as metallic particles and plastic particles. Particles may be organism components, such as a cast, other than cells, or may be cells such as microorganism cells, animal cells, or plant cells. The specimen containing particles is not limited as long as it is a liquid (in either an undiluted form or a diluted form) containing particles. Preferably, the specimen is, for example, a cell culture specimen or an organism-derived specimen. The cell culture specimen is, for example, a sample containing in-vitro cultured cells. Examples of the organism-derived specimen may include liquid specimens derived from an organism, such as peripheral blood, cord blood, bone marrow, cerebrospinal fluid, ascitic fluid, pleural fluid, interstitial fluid, and urine. The organism-derived specimen is preferably peripheral blood, cord blood, or bone marrow.

Examples of reagents include a particle detection reagent, a hemolyzing agent, a washing liquid, a cell membrane permeable agent, a diluent, a cell immobilization component, and RNase, which are needed for preparation of a measurement sample according to analysis of measurement target particles. Regarding the particle detection reagent, each reagent contains at least one type of labeling substance. The labeling substance is not limited as long as it allows detection of particles. The particle detection reagent is preferably a cell detection reagent. The labeling substance is preferably a cell labeling substance. The particle detection reagent preferably contains at least one type of cell labeling substance selected from the group consisting of: one or more nucleic acid labeling substances which label nucleic acid; and one or more protein labeling substances which label protein. Examples of the nucleic acid labeling substances preferably include nucleic acid stain substances such as ethidium bromide (EB), acridine orange (AO), propidium iodide (PI), 7-amino-actinomycin D (7-AAD), 4',6-diamidino-2-phenyl indole (DAPI), Hoechst 33342 (2'-(4-ethoxyphenyl)-5-(4-methyl-1-piperazinyl)-2,5'-bi-1H-benzimidazole trihydrochloride), ethidium homodimer-1, ethidium homodimer-2, ethidium monoazide, trimethylenebis[[3-[[4-[[(3-methylbenzothiazole-3-ium)-2-yl]methylene]-1,4-dihydroquinoline]-1-yl]propyl]dimethylaminium].tetraiodide (TOTO-1), 4-[(3-methylbenzothiazole-2(3H)-ylidene) methyl]-1-[3-(trimethylaminio)propyl]quinolinium.diiodide (TO-PRO-1), N,N,N',N'-tetramethyl-N,N'-bis[3-[4-[3-[(3-methylbenzothiazole-3-ium)-2-yl]-2-propenylidene]-1,4-dihydroquinoline-1-yl]propyl]-1,3-propanediaminium.tetraiodide (TOTO-3), 2-[3-[[1-[3-(trimethylaminio)propyl]-1,4-dihydroquinoline]-4-ylidene]-1-propenyl]-3-methylbenzothiazole-3- ium.diiodide (TO-PRO-3), and fluorescent dyes represented by structural formula (IV) below.

[Chemical formula 1]

(IV)

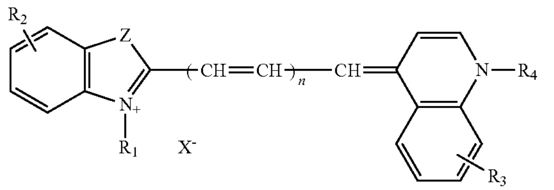

In the formula above, $R_1$ and $R_4$ each are a hydrogen atom, an alkyl group, an alkyl group having a hydroxy group, an alkyl group having an ether group, an alkyl group having an ester group, or a benzyl group that may have a substituent; $R_2$ and $R_3$ each are a hydrogen atom, a hydroxyl group, a halogen, an alkyl group, an alkenyl group, an alkynyl group, or an alkoxy group; Z is a sulfur atom, an oxygen atom, or a carbon atom having a methyl group; n is 0, 1, 2, or 3; and $X^-$ is an anion.

In structural formula (IV), in a case where either one of $R_1$ and $R_4$ is an alkyl group having 6 to 18 carbon atoms, the other is preferably an hydrogen atom or an alkyl group having less than 6 carbon atoms. Among alkyl groups having 6 to 18 carbon atoms, an alkyl group having 6, 8, or 10 carbon atoms is preferable. Examples of the substituent of the benzyl group represented by $R_1$ and $R_4$ include alkyl groups having 1 to 20 carbon atoms, alkenyl groups having 2 to 20 carbon atoms, and alkynyl groups having 2 to 20 carbon atoms. Among these, a methyl group or an ethyl group is particularly preferable. Examples of the alkenyl group represented by $R_2$ and $R_3$ include alkenyl groups having 2 to 20 carbon atoms. Examples of the alkoxy group represented by $R_2$ and $R_3$ include alkoxy groups having 1 to 20 carbon atoms. Among these, a methoxy group or an ethoxy group is particularly preferable. Examples of the anion $X^-$ include: halogen ions such as $F^-$, $Cl^-$, $Br^-$, and $I^-$; $CF_3SO_3^-$; and $BF_4^-$.

Examples of the nucleic acid labeling substance may include a nucleic acid probe labeled with fluorescence, and a nucleotide labeled with fluorescence. Examples of the protein labeling substance may include: a protein that is labeled with a fluorescence substrate and can bind to a target protein; and a vitamin that is labeled with a fluorescence substrate and can bind to a target protein. Examples of the protein that binds to a target protein may include a ligand, an antibody, a lectin, and a lipid-bound protein (preferably, a phospholipid-bound protein) each binding to a receptor. The fluorescent substance is not limited as long as it can be detected by a measurement section 2. The fluorescent substance is preferably a substance that can be used for flow cytometry.

Particle detection reagents set in a reagent setting unit 35 of a reagent preparing apparatus 1 described later preferably correspond to a plurality of labeling substances. "Corresponding to labeling substances" may be a situation in which one particle detection reagent contains a plurality of labeling substances, or may be a situation in which a plurality of particle detection reagents each containing one or more labeling substances are provided.

Each particle detection reagent or each labeling substance is preferably mixed with particles contained in a specimen at an appropriate mixing ratio. The mixing ratio may vary among the respective particle detection reagents or the respective labeling substances. Further, in a case where a plurality of types of particles are contained in one specimen, the mixing ratio is determined in consideration of the ratio of particles to be measured.

In the following embodiments, particles to be measured are cells. However, the sample preparing apparatus and the particle analyzer are not limited to use for analysis of cells.

Structures of Sample Preparing Apparatus and Particle Analyzer

FIG. 1 shows a schematic structure of a particle analyzer 100 according to the present embodiment. The particle analyzer 100 of the present embodiment includes a sample preparing apparatus 1, an analysis section 5, a display section 8, an input section 9, and an output section 10. The sample preparing apparatus 1 of the present embodiment includes: a measurement section 2 which performs pre-measurement of a specimen and main measurement of a measurement sample; a sample preparation section 3 which performs concentration adjustment for a specimen and preparation of a measurement sample; and a control section 4 which controls the measurement section 2 and the sample preparation section 3. The analysis section 5 performs, for example, analysis of measurement data obtained by main measurement of the measurement section 2.

Structure of Measurement Section

The measurement section 2 performs pre-measurement on a specimen to obtain information relating to the viscosity of the specimen (viscosity information including a hematocrit value, the number of red blood cells per unit volume, the number of white blood cells per unit volume, the number of platelets per unit volume, a mean corpuscular volume value, etc., of the specimen). The measurement section 2 also functions as a pre-measurement section which performs pre-measurement of the specimen to detect the number of measurement target cells that are contained in the specimen. Further, the measurement section 2 of the present embodiment also functions as a main measurement section which performs main measurement of a measurement sample to detect information relating to the properties of the measurement target cells, which is used for cell analysis by the analysis section 5.

The measurement section 2 includes: a first measurement section 2*a* which obtains the information relating to the viscosity of the specimen; and a second measurement section 2*b* which detects the measurement target cells in the specimen, and performs main measurement of the measurement sample. The first measurement section 2*a* can adopt electric resistance type detection means that detects a pulse voltage on the basis of the Ohm's law. The second measurement section 2*b* can adopt a flow cytometer. The first measurement section 2*a* may include both electric resistance type detection means and flow cytometry type detection means. By obtaining the viscosity information of the specimen through the pre-measurement of the specimen, the specimen can be accurately dispensed when the measurement sample is prepared. In addition, when the measurement sample is prepared, even if a user does not separately obtain viscosity information, at least process steps from obtainment of the viscosity information to preparation of the measurement sample can be automatically performed. The sample preparing apparatus 1 of the present embodiment need not necessarily perform the pre-measurement of the specimen. A pre-measurement apparatus for pre-measurement may be provided separately from the sample preparing apparatus 1, and the sample preparing apparatus 1 may obtain, through the input section 9 or communication, only measurement values that are obtained in the pre-measurement apparatus.

Figure 2:
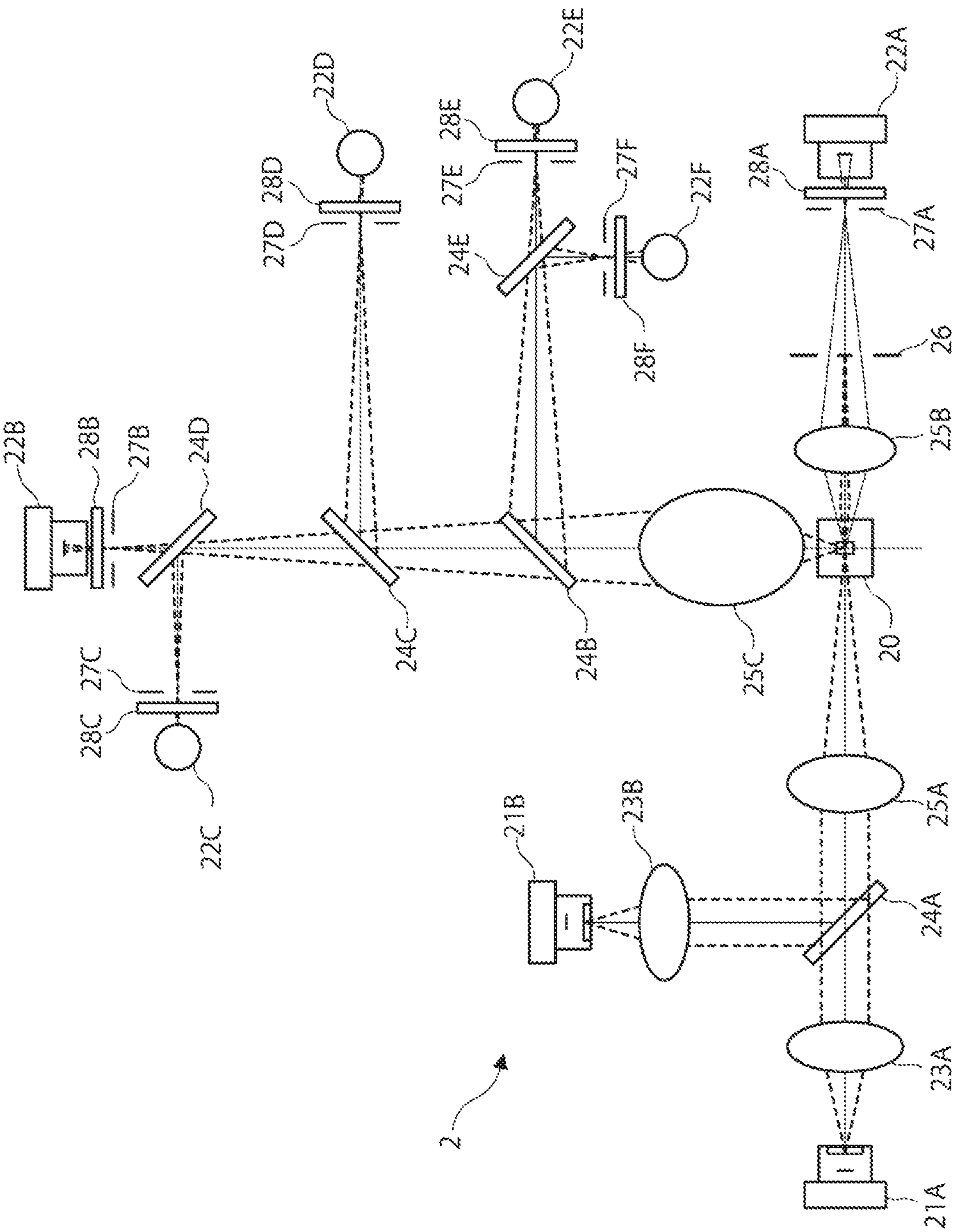
FIG. 2 is a schematic diagram of an optical system of a flow cytometer.
Figure 3:
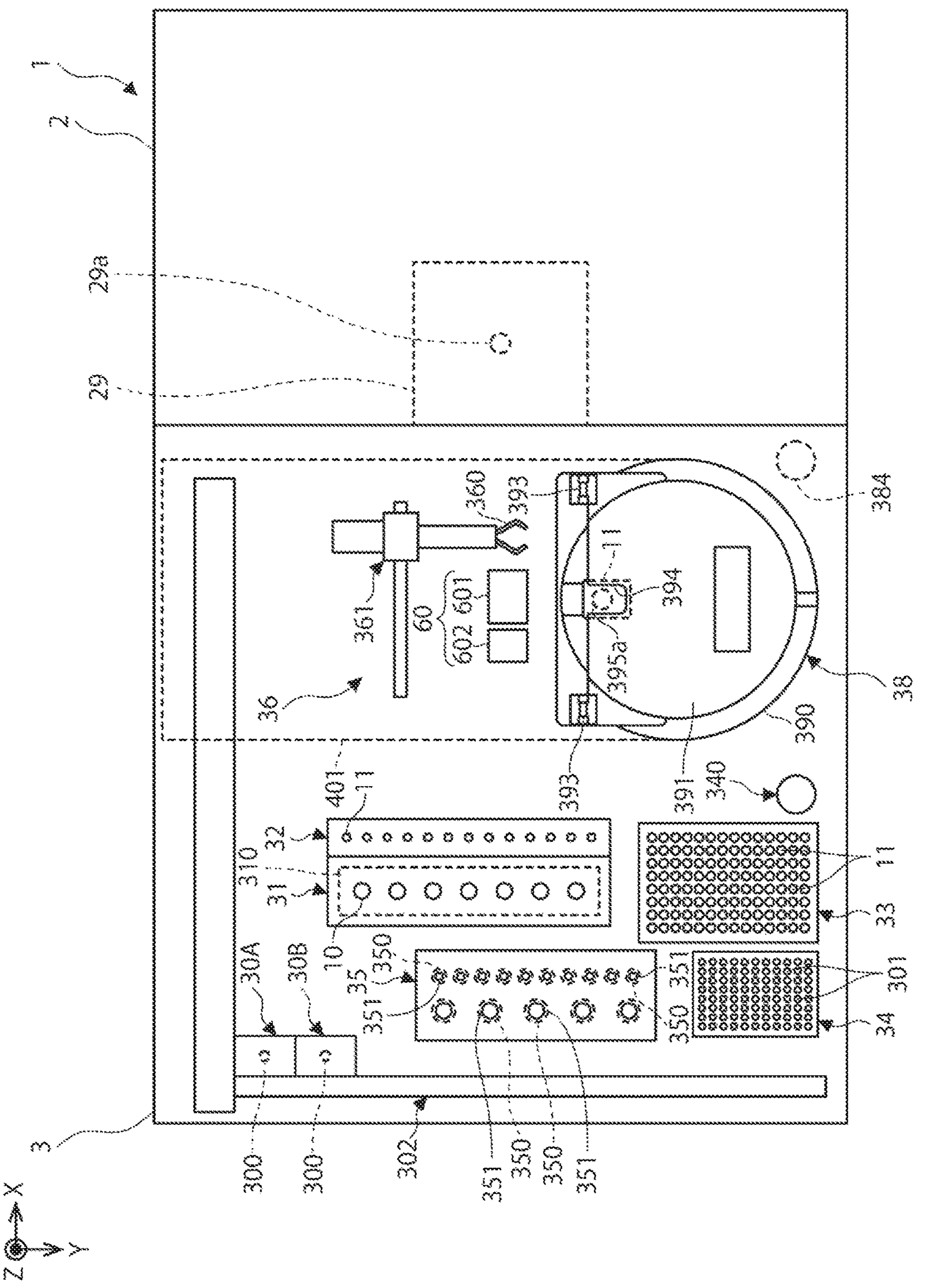
FIG. 3 is a schematic configuration diagram of a reagent preparing apparatus.

FIG. 2 is a schematic diagram showing an optical system of a flow cytometer constituting the second measurement section 2*b*. The flow cytometer includes: a flow cell 20 through which a specimen passes; light sources 21A and 21B each applying light to the specimen passing through the flow cell 20; and light receiving elements 22A to 22F each detecting optical information of light derived from a particle in the specimen, and outputting a detection signal obtained by converting the optical information into an electric signal.

The optical information is information included in one or more light wavelength spectrums emitted from a particle. The light wavelength spectrum includes: individual light wavelengths included in the light wavelength spectrum; light wavelength regions; and the intensities of lights having the respective light wavelengths or the intensities of lights in the respective light wavelength regions.

Light emitted from the light source 21A is applied to the flow cell 20 through a collimator lens 23A, a dichroic mirror 24A, and a condenser lens 25A. Forward scattered light of light derived from a particle passing through the flow cell 20 is condensed by the condenser lens 25B, and enters the light receiving element 22A through a beam splitter 26, a pinhole plate 27A, and a bandpass filter 28A.

Meanwhile, side scattered light and side fluorescence of the light derived from the particle passing through the flow cell 20 are condensed by a condenser lens 25C. The side scattered light enters the light receiving element 22B through dichroic mirrors 24B to 24D, a pinhole plate 27B, and a bandpass filter 28B. The side fluorescence having a wavelength not shorter than 520 nm and not longer than 542 nm passes through the dichroic mirrors 24B and 24C, is reflected by the dichroic mirror 24D, and enters the light receiving element 22C through a pinhole plate 27C and a bandpass filter 28C. The side fluorescence having a wavelength not shorter than 570 nm and not longer than 620 nm passes through the dichroic mirror 24B, is reflected by the dichroic mirror 24C, and enters the light receiving element 22D through a pinhole plate 27D and a bandpass filter 28D. Further, the side fluorescence having a wavelength not shorter than 670 nm and not longer than 800 nm is reflected by the dichroic mirror 24B, passes through a dichroic mirror 24E, and enters the light receiving element 22E through a pinhole plate 27E and a bandpass filter 28E.

Light emitted from the light source 21B is applied to the flow cell 20 through a collimator lens 23B, the dichroic mirror 24A, and the condenser lens 25A. Side fluorescence of light derived from a particle passing through the flow cell 20 is condensed by the condenser lens 25C. The side fluorescence having a wavelength not shorter than 662.5 nm and not longer than 687.5 nm is reflected by the dichroic mirror 24B, and is reflected by the dichroic mirror 24E, and then enters the light receiving element 22F through a pinhole plate 27F and a bandpass filter 28F.

For example, the light source 21A is implemented by a laser diode having a wavelength of 488 nm, and the light source 21B is implemented by a laser diode having a wavelength of 642 nm. The flow cell 20 is implemented by a sheath flow cell. The light receiving element 22A for receiving the forward scattered light is implemented by a photodiode, the light receiving element 22B for receiving the side scattered light is implemented by an avalanche photodiode (APD), and each of the light receiving elements 22C to 22F for receiving the side fluorescence is implemented by a photomultiplier tube (PMT). In FIG. 2, the flow cytometer includes six light receiving elements 22A to 22F. Among them, four light receiving elements 22C to 22F respectively detect optical information of four lights that are derived from dyes binding to particles in the specimen, and have different peak wavelengths. However, the present invention is not limited thereto. The flow cytometer may include three or more light receiving elements, and at least two or more light receiving elements among the three or more light receiving elements may be configured to detect optical information of lights that are derived from at least two dyes and have different peak wavelengths, respectively.

One light source or two or more light sources may be provided. For example, the number of light sources may be selected from integers between 1 to 10. Light sources are selected in accordance with wavelength regions of lights derived from dyes that bind to particles. When two or more light sources are provided, these light sources preferably emit lights having different peak wavelengths. Providing two or more light sources is more preferable than providing one light source because, in this case, a plurality of fluorescences can be separately detected with high accuracy. Meanwhile, when two light sources are used, a plurality of fluorescences can be separately detected by shifting emission timings of lights from the respective light sources. By using dyes suitable for the peak wavelengths of the lights from the respective light sources, overlapped portions of the respective wavelength regions of the plurality of fluorescences can be reduced. Each light source is not limited as long as light in a wavelength region to be detected is emitted from a particle. For example, one or more types of light sources selected from the group consisting of a halogen lamp, an LED (Light emitting diode) lamp, a gas laser, and a laser diode (semiconductor laser) can be used. The numbers of the photodiodes, the dichroic mirrors, and the bandpass filters can be changed in accordance with the number of peak wavelengths of lights derived from particles. In addition, the types of the photodiodes, the dichroic mirrors, and the bandpass filters can also be selected in accordance with peak wavelengths of lights derived from particles, or wavelength regions of the lights, and the intensities of the lights.

The detection signals outputted from the respective light receiving elements 22A to 22F are amplified by a preamplifier (not shown), and transmitted to a signal processing section 6 (shown in FIG. 1). The signal processing section 6 is composed of a signal processing circuit that performs signal processing necessary for the detection signals outputted from the measurement section 2.

Figure 17:
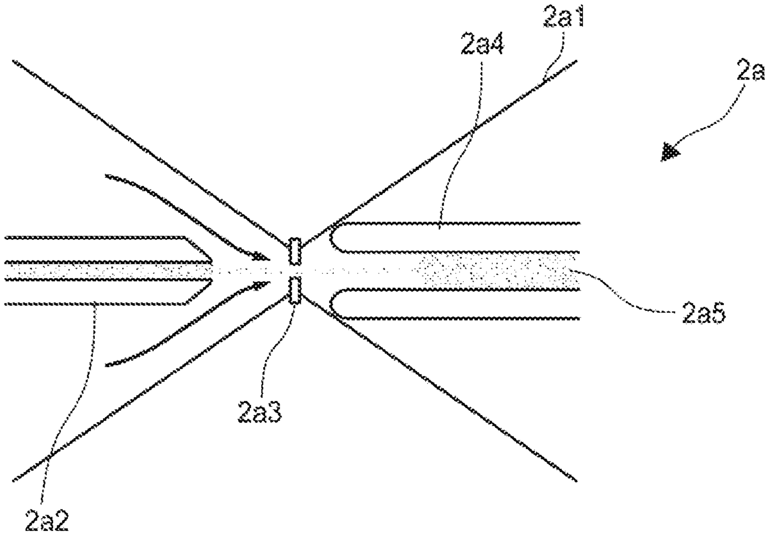
FIG. 17 is a schematic diagram showing a sheath flow DC detection means.

FIG. 17 is a schematic diagram showing a detection system of the first measurement section 2*a* including electric resistance type detection means (sheath flow DC detection means). The first measurement section 2*a* includes: a conical chamber 2*a*1; a sample nozzle 2*a*2 from which a diluted sample obtained by diluting a specimen with a diluent is pushed out; an aperture (electric resistance type detector) 2*a*3 which detects a particle; and a recovery tube 2*a*4 which recovers the diluted sample having passed through the aperture 2*a*3. A particle 2*a*5 contained in the diluted sample is pushed out from the sample nozzle 2*a*2. Thereafter, the particle 2*a*5 is surrounded by a front sheath liquid that flows in directions indicated by arrows, and passes through the aperture. In the aperture 2*a*3, a voltage is applied to the diluted sample passing therethrough, and electric resistance of a non-electroconductive particle is changed when the particle passes through the aperture 2*a*3. The voltage at the aperture 2*a*3 is transmitted to the signal processing section 6 (shown in FIG. 1). The signal processing section 6 extracts a waveform corresponding to the particle on the basis of the signal outputted from the aperture 2*a*3, and transmits a peak value of the waveform as particle information to the control section.

In the first measurement section 2*a*, information as follows can be obtained: the number of particles such as the number of red blood cells or the number of platelets; a mean particle volume such as a mean corpuscular volume (a mean value of the sizes of red blood cells in whole blood: MCV); and the like. A hematocrit value is the ratio of the volume of blood cell components to the volume of whole blood. When the specimen is peripheral blood, since most of the volume of the blood cell components is occupied by the volume of red blood cells, a hematocrit value can be calculated by a red-blood-cell pulse height detection method, using the MCV and the number of red blood cells in whole blood which are measured in the first measurement section 2*a*. Specifically, a hematocrit value is calculated by multiplying the MCV by the number of red blood cells in whole blood, and dividing the resultant value by the volume of whole blood.

Structure of Sample Preparation Section

As shown in FIG. 1 and FIGS. 3 to 7, the sample preparation section 3 adjusts the concentration of measurement target cells in a specimen used for preparation of a measurement sample, and prepares a measurement sample from the specimen and one or a plurality of cell detection reagents selected from among a plurality of cell detection reagents. The structure of the sample preparation section 3 described below is merely an example, and the sample preparation section 3 is not limited to the structure described below.

The sample preparation section 3 includes a specimen dispenser 30A, a reagent dispenser 30B, a specimen container setting unit 31, a dispensing tube setting unit 32, a dispensing tube storage unit 33, a pipette tip storage unit 34, a reagent setting unit 35, a tube transfer unit 36, specimen liquid amount detecting means 37, a centrifuge 38, and a reception unit 39. In FIGS. 3 to 6, X, Y, and Z axes are orthogonal to each other. The X axis represents a left-right direction, the Y axis represents a front-rear direction, and the Z axis represents a vertical direction.

The specimen dispenser 30A and the reagent dispenser 30B each have a nozzle 300. For example, a disposal plastic pipette tip 301 is attached to each nozzle 300. The pipette tip 301 is not necessarily used. In the specimen dispenser 30A, the nozzle 300 performs dispensing of the specimen via the pipette tip 301 (aspiration of the specimen from a specimen container, and discharge of the aspirated specimen to a dispensing tube), whereby a predetermined amount of the specimen is aspirated from a specimen container 10 set in the specimen container setting unit 31, and a predetermined amount of the specimen is discharged into a dispensing tube 11. Dispensing of the specimen by the specimen dispenser 30A is controlled in accordance with predetermined dispensing conditions described later. In the reagent dispenser 30B, the nozzle 300 performs aspiration and discharge of a liquid via the pipette tip 301, whereby a predetermined amount of a reagent is aspirated from a reagent container 350 set in the reagent setting unit 35, and a predetermined amount of the reagent is discharged into a dispensing tube 11. The amounts (volumes) of the specimen and the reagent aspirated by the corresponding nozzles 300 can be obtained from flow rate sensors (not shown) provided in the respective dispensers 30A and 30B. Each of the dispensers 30A and 30B is provided with nozzle transfer means 302 for moving the nozzle 300 in the XYZ-axis directions. The nozzle transfer means 302 moves the nozzle 300 by driving a motor (not shown).

In the specimen dispenser 30 of the present embodiment, as the specimen liquid amount detecting means 37 for detecting the liquid amount of the specimen contained in the specimen container 10, a specimen liquid level detecting sensor (not shown) is provided, which senses a liquid level of the specimen in the specimen container 10 when the nozzle 300 is located directly above the specimen container 10 in the specimen container setting unit 31. By sensing the liquid level of the specimen in the specimen container 10, the liquid amount of the specimen (the amount of the specimen) contained in the specimen container 10 can be calculated. The specimen dispenser 30 may be provided with intra-nozzle liquid amount detecting means 30A1 for detecting the liquid amount of the specimen aspirated by the nozzle 300, as a liquid amount detecting unit for detecting the liquid amount of the dispensed specimen. An example of the intra-nozzle liquid amount detecting means 30A1 may be an intra-nozzle liquid level detecting sensor (not shown) which detects, at least, the liquid level of the specimen in the nozzle when the nozzle 300 aspirates the specimen and the liquid level of the specimen in the nozzle when the nozzle 300 discharges the specimen. In the case where the specimen that has been aspirated by one aspiration of the nozzle 300 is dividedly discharged into a plurality of dispensing tubes 11, the intra-nozzle liquid level detecting sensor senses the liquid level every time discharge of the specimen is performed, thereby detecting change in the liquid level. By sensing the liquid level of the specimen in the nozzle 300, the liquid amount of the specimen aspirated by the nozzle (aspiration amount) and the liquid amount of the specimen discharged (discharge amount) can be calculated, whereby the liquid amount of the specimen (the amount of the specimen) dispensed can be calculated, and specimen dispensing accuracy can be monitored.

A specimen container 10 containing a specimen collected from a subject is set in the specimen container setting unit 31. A plurality of specimen containers 10 can be set in the specimen container setting unit 31. A dispensing tube 11 as a mixing container for containing a prepared sample is set in the dispensing tube setting unit 32. The dispensing tube 11 is also used for containing a specimen to be used for measurement by the measurement section 2. A plurality of dispensing tubes 11 can be set in the dispensing tube setting unit 32. The dispensing tube setting unit 32 may be provided with dispensed liquid amount detecting means (not shown) for detecting the liquid amount of the specimen discharged into each dispensing tube 11, as a liquid amount detecting unit for detecting the liquid amount of the dispensed specimen. An example of the dispensed liquid amount detecting means is a liquid level detecting sensor which detects the liquid level of the specimen discharged into the dispensing tube 11. Another example of the dispensed liquid amount detecting means is a weight detecting sensor which detects the weight of the specimen discharged into the dispensing tube 11. For example, in a case where the specimen is peripheral blood, since the blood density is about 1.06 mg/μl, 53 mg of peripheral blood is equivalent to about 50 μl. Therefore, by detecting the weight of the specimen in each dispensing tube 11, the liquid amount of the specimen in each dispensing tube 11 can be calculated. By detecting the liquid amount of the specimen in each dispensing tube 11, the liquid amount of the specimen (the amount of the specimen) dispensed can be calculated, and the specimen dispensing accuracy can be monitored.

The specimen container setting unit 31 has specimen temperature adjusting means 310 such as a heating device or a cooling device therein. The specimen temperature adjusting means 310 allows the temperature of the specimen in the specimen container 10 to be maintained at a temperature suitable for the specimen. The cooling device is implemented by, for example, a peltier device, a compressor, or the like. The heating device is implemented by, for example, a block heater or other heaters. The temperature inside the specimen container setting unit 31 is measured by a temperature sensor (not shown).

The dispensing tube storage unit 33 is stocked with a plurality of dispensing tubes 11. Each of the dispensing tubes 11 in the dispensing tube storage unit 33 is transferred to and set in the dispensing tube setting unit 32 by the tube transfer unit 36.

The pipette tip storage unit 34 is stocked with a plurality of pipette tips 301 to be attached to the nozzles 300. The pipette tip storage unit 34 is stocked with pipette tips 301 having different sizes. Any of large-sized and small-sized pipette tips 301 can be attached to the nozzles 300. To each nozzle 300, a pipette tip 301 having a size according to the dispensing amount of the specimen or the reagent is attached. The pipette tips 301 that have been used are discarded into a disposal unit 340.

The reagent setting unit 35 is a reagent storage in which a plurality of reagents are stored. A plurality of reagent containers 350 containing the reagents are set in the reagent setting unit 35. The reagent setting unit 35 has a plurality of openings 351 formed therein, and the reagent containers 350 are set beneath the respective openings 351. Aspiration of the reagent can be performed by causing the nozzle 300 of the reagent dispenser 30B to enter the reagent container 350 from the opening 351.

A plurality of cell detection reagents are set in the reagent setting unit 35. At least one type of cell labeling substance contained in each cell detection reagent is preferably different among the respective cell detection reagents. A combination of a plurality of cell detection reagents to be set in the reagent setting unit 35 at one time can be a combination that encompasses cell labeling substances capable of detecting a group of cell markers required for specifying a type of leukemia, for example. Each cell detection reagent may contain a buffer solution in addition to the cell labeling substance. The buffer solution may contain a salt such as sodium chloride. The salt is preferably added such that the prepared measurement sample becomes isotonic with the inside of the cell. Each cell detection reagent may further contain a cell immobilization component such as methanol or paraformaldehyde. Each cell detection reagent may contain RNase or the like.

In the reagent setting unit 35, reagents, other than the cell detection reagents, which are required for preparation of a measurement sample according to analysis of measurement target cells, such as a hemolyzing agent, a washing liquid, a cell membrane permeable agent, a diluent, the cell immobilization component, and RNase can be set in addition to the cell detection reagents. The diluent contains at least a buffer solution, and may contain salt such as sodium chloride as appropriate. The salt may be added such that the prepared measurement sample is isotonic with the inside of the cell. The diluent may contain a hemolyzing agent that hemolyzes red blood cells. The hemolyzing agent preferably does not dissolve nucleated cells such as white blood cells. Examples of the hemolyzing agent preferably include an aqueous solution containing a surfactant, a citrate buffer solution, HEPES, phosphate and buffer solution. The surfactant may be any of an anionic surfactant, a cationic surfactant, a bipolar surfactant, a nonionic surfactant, a natural surfactant, and the like. One hemolyzing agent may contain a plurality of types of surfactants. More preferably, examples of the hemolyzing agent may include: a hemolyzing agent that contains a cationic surfactant and an organic acid, and has a pH within a range of 4.5 to 11.0; a hemolyzing agent that contains a nonionic surfactant and an organic acid, and has a pH within a range of 4.5 to 11.0; and a hemolyzing agent that contains an anionic surfactant and a natural surfactant, and has a pH within a range of 4.5 to 11.0. The range of the pH described above is preferably 6.0 to 8.0. Each of these hemolyzing agents may further contain: alcohol such as methanol, ethanol, or phenoxyethanol; a fixative such as formaldehyde; a chelating agent; sodium azide; and the like. Specific examples of the hemolyzing agent may include: an ammonium chloride-based hemolyzing agent (pH 7.3, 1.68 M of ammonium chloride, 100 mM of potassium bicarbonate, 0.82 mM of EDTA 2K); a cell immobilizing hemolyzing agent (pH 7. formaldehyde 3, 10%, 3.5% of methanol, 30% of diethylene glycol, 100 mM of citric acid); and a cell membrane permeable hemolyzing agent (pH 7.3, not more than 1% of phenoxyethanol, not more than 1% of saponin, not more than 1% of N-Lauryl sarcosine sodium salt, not more than 1% of sodium azide). The cell membrane permeable hemolyzing agent can be also used as a cell membrane permeable agent when detecting protein in the cell.

Each of the reagent containers 350 set in the reagent setting unit 35 has, attached thereto, a barcode, a tag, or the like in which information relating to the corresponding reagent is stored. The information relating to the reagent includes identification information (ID) for identifying the reagent. The information relating to the reagent may include the name of a measurement item, and the like. The reagent setting unit 35 is provided with the reception unit 39 (shown in FIG. 1) such as a barcode reader or an RFID reader capable of reading the barcode or the like. By reading the barcodes or the like attached to the reagent containers 350, information relating to the cell detection reagents and the reagents other than the cell detection reagents, which are set in the reagent setting unit 35, can be obtained.

The reagent setting unit 35 may have, therein, reagent temperature adjusting means (not shown) for keeping the temperature of the reagent contained in each reagent container 350 at a desired temperature. The reagent temperature adjusting means is a cooling device capable of cooling the reagent in each reagent container 350 and/or a heating device capable of heating the reagent in each reagent container 350. The temperature inside the reagent setting unit 35 can be measured by a temperature sensor (not shown).

The tube transfer unit 36 includes: a gripper 360 which holds a dispensing tube 11; and movement means 361 which moves the gripper 360 in the XYZ axis directions. The movement means 361 moves the gripper 360 by driving a motor (not shown). Each dispensing tube 11 in the dispensing tube setting unit 32 is moved while being held by the gripper 360, and thus conveyed to the centrifuge 38 or the measurement section 2.

The centrifuge 38 performs a preparation process of preparing a measurement sample from a specimen and a predetermined reagent. The centrifuge 38 also performs a concentration adjustment process of adjusting the concentration of measurement target cells in the specimen. That is, in the present embodiment, the centrifuge 38 functions as a concentration adjustment unit.

The centrifuge 38 is provided in a housing including: a bottomed cylindrical main chamber 390; a lid 391 covering an upper opening of the main chamber 390; and a temperature adjustment chamber 392 provided beneath the main chamber 390. The lid 391 is mounted to the main chamber 390 via a hinge 393. The lid 391 has, formed therein, a first entrance port 394 through which the nozzle 300 enters the main chamber 390 from above. The first entrance port 394 allows the nozzle 300 of each of the dispensers 30A and 30B to enter the main chamber 390. The nozzle 300 enters the main chamber 390 through the first entrance port 394, and discharges the specimen or the reagent into the dispensing tube 11 held in the centrifuge 38 in the main chamber 390, or aspirates the liquid in the dispensing tube 11.

Figure 5A:
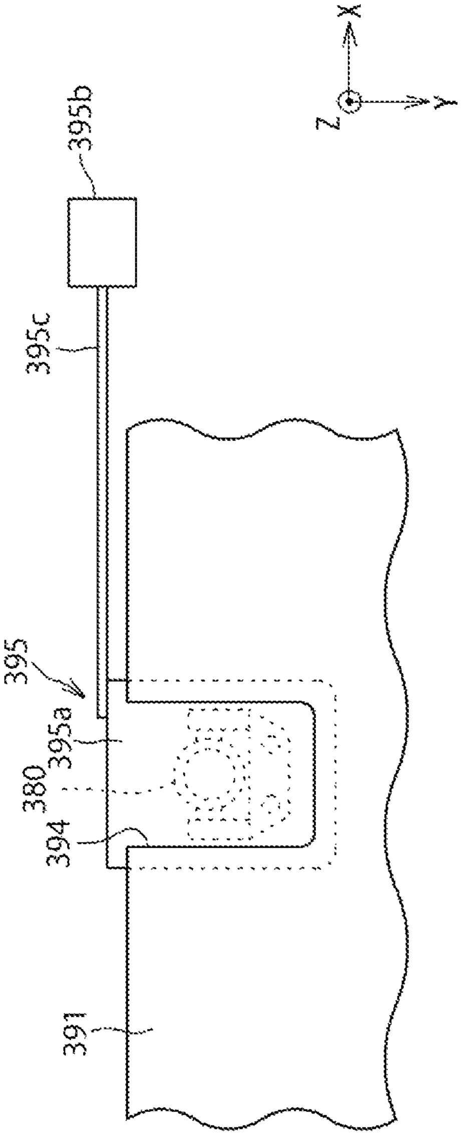
FIGS. 5A and 5B are partially enlarged views of the sample preparation section.
Figure 5B:
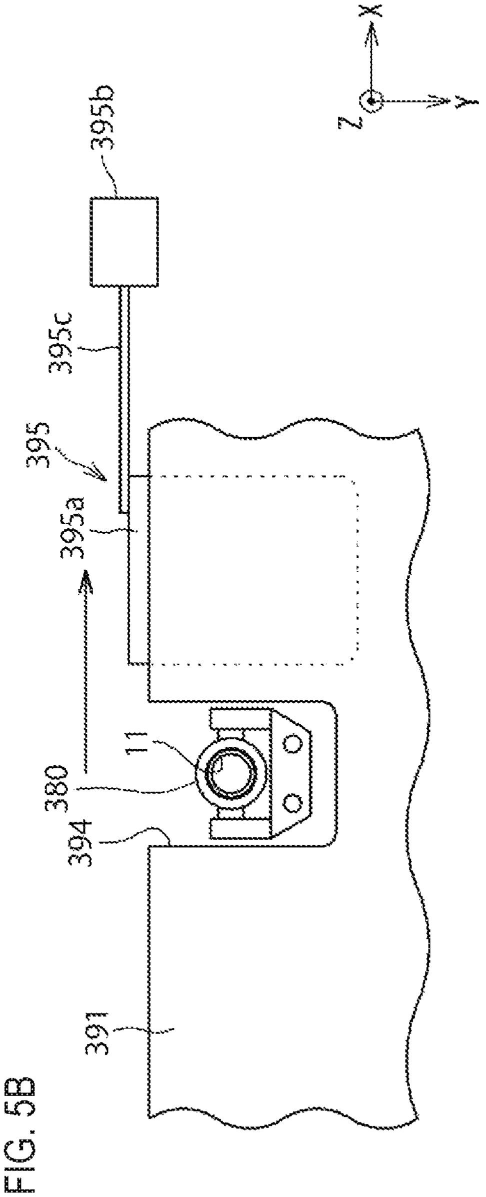
Figure 6:
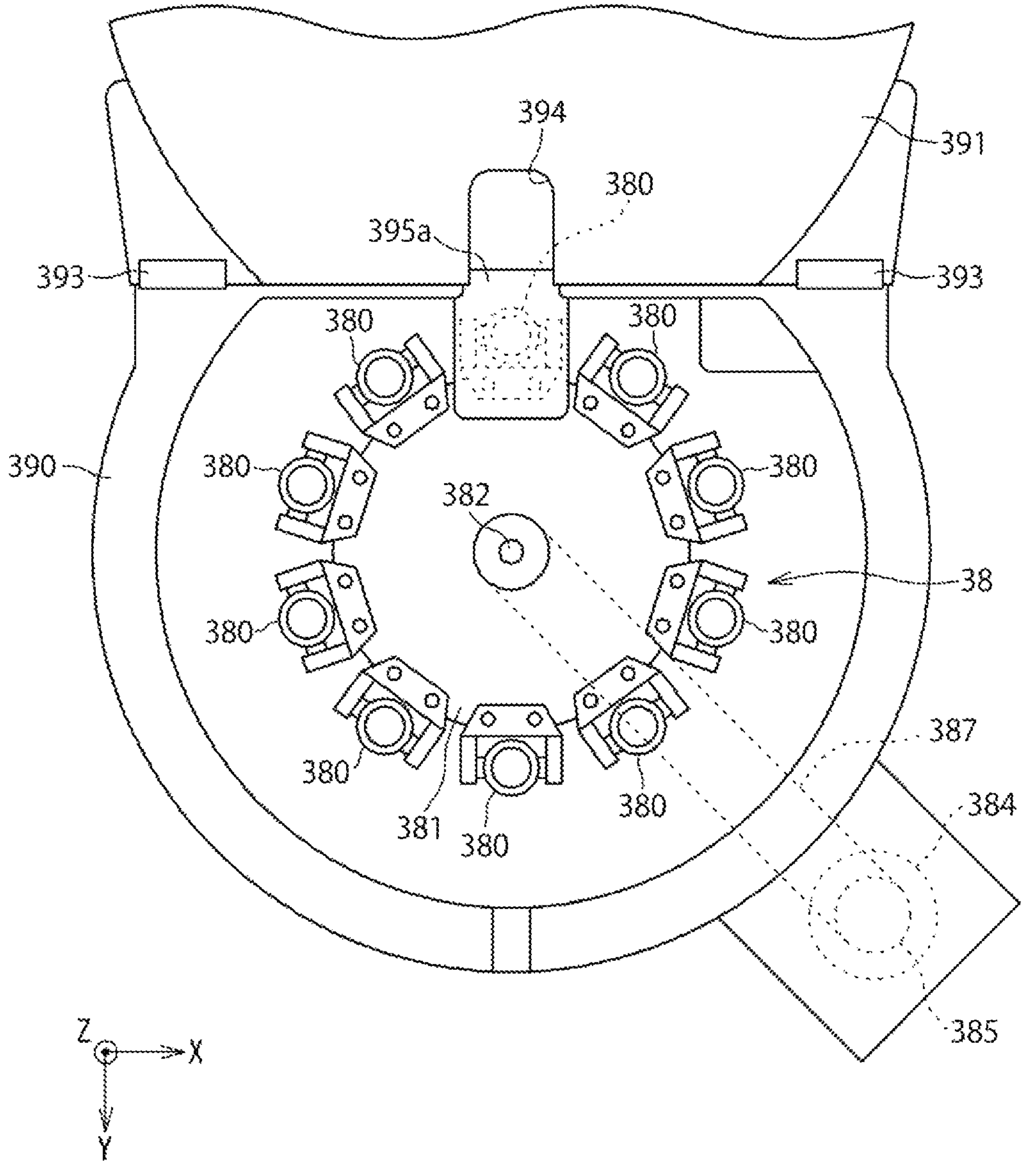
FIG. 6 is a plan view of a centrifuge.
Figure 7:
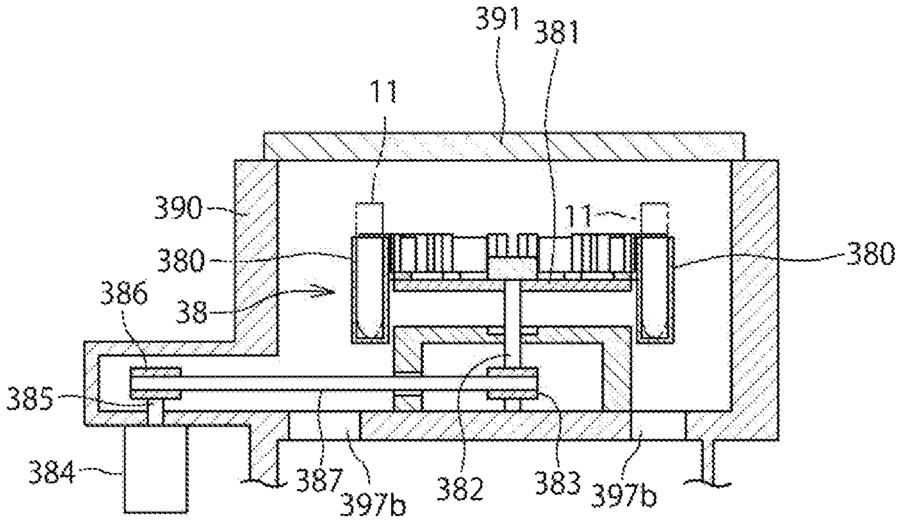
FIG. 7 is a partially cross-sectional view of the sample preparation section.

The main chamber 390 has opening/closing means 395 for opening and closing the first entrance port 394. The opening/closing means 395 according to the present embodiment is composed of: a shutter 395*a* which closes the first entrance port 394; a drive part 395*b* which causes the shutter 395*a* to perform opening/closing operation; and a connection part 395*c* which connects the shutter 395*a* and the drive part 395*b*. The drive part 395*b* is, for example, a solenoid, and moves the shutter 395*a* in the Y axis direction. As shown in FIG. 5A, when the first entrance port 394 is closed by the shutter 395*a*, the inside of the main chamber 390 is substantially hermetically sealed, whereby temperature change in the main chamber 390 can be inhibited. As shown in FIG. 5B, when the shutter 395*a* is moved and the first entrance port 394 is opened, the nozzle 300 is allowed to enter the main chamber 390 from the first entrance port 394.

Figure 4:
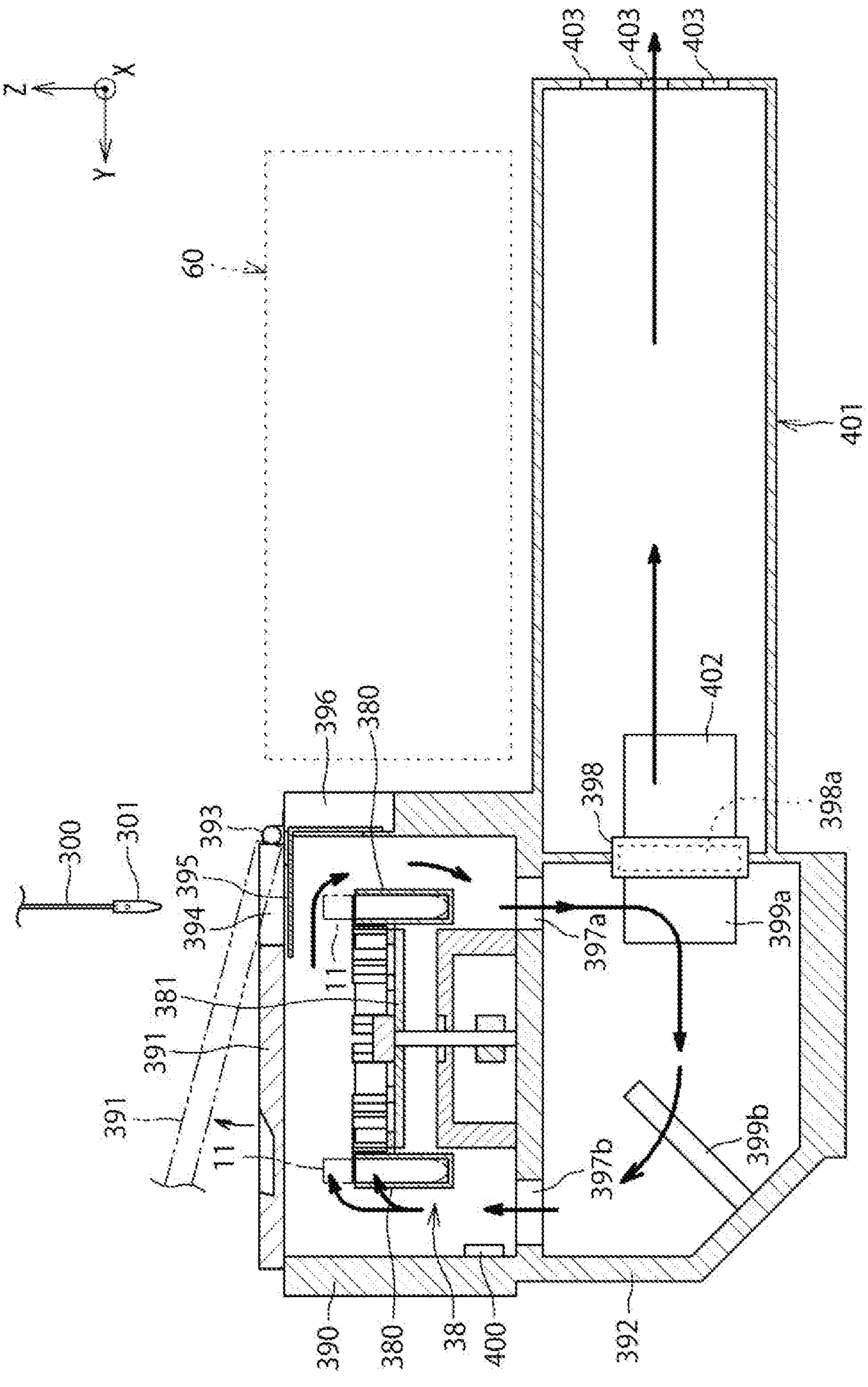
FIG. 4 is a cross-sectional view of a sample preparation section.

As shown in FIG. 4, the main chamber 390 has, formed therein, a second entrance port 396 through which the gripper 360 enters the main chamber 390 from the rear. The second entrance port 396 allows the gripper 360 of the tube transfer unit 36 to enter the main chamber 390. The gripper 360 enters the main chamber 390 through the second entrance port 396, and sets the dispensing tube 11 in a holder 380 in the centrifuge 38, or takes out the dispensing tube 11 from the holder 380 in the centrifuge 38. The shutter 395*a* is formed in an L shape in a cross-sectional view so that it can close the second entrance port 396 as well as the first entrance port 394.

The centrifuge 38 is provided with a plurality of holders 380 for holding dispensing tubes 11, and a rotor 381 having an outer circumference to which the plurality of holders 380 are attached. Rotation of the rotor 381 causes the liquid in the dispensing tube 11 held by each holder 380 to be centrifuged. The rotor 381 rotates around a rotation shaft 382 which is rotatably supported at a bottom portion of the main chamber 390. A first pulley 383 is provided at a lower portion of the rotation shaft 382. A second pulley 386 is provided at a rotation shaft 385 of a motor 384 which drives the rotation shaft 382 to rotate. An endless belt 387 is wound around and between the first pulley 383 and the second pulley 386. Rotation of the motor 384 is transmitted to the rotation shaft 382 via the first pulley 383, the endless belt 387, and the second pulley 386, thereby rotating the rotor 381. The motor 384 is disposed outside the sample preparation section 8.

The temperature adjustment chamber 392 is partitioned from the main chamber 390 by the bottom portion of the main chamber 390. Through-holes 397*a* and 397*b* are formed in the bottom portion of the main chamber 390. The through-holes 397*a* and 397*b* allow the main chamber 390 and the temperature adjustment chamber 392 to communicate with each other.

In the temperature adjustment chamber 392, temperature adjusting means 398 which adjusts the atmospheric temperature inside the main chamber 390 is provided. The temperature adjusting means 398 has a Peltier device 398*a*, for example. Further, in the temperature adjustment chamber 392, convection generating means 399*a* and 399*b* are provided, which generate convection that circulates in the main chamber 390 and the temperature adjustment chamber 392 through the through-holes 397*a* and 397*b*. The convection generating means 399*a* and 399*b* are implemented by, for example, fans or the like. Cold or hot air generated from the temperature adjusting means 398 is sent from the temperature adjustment chamber 392 to the main chamber 390 by means of air current generated by the convection generating means 399*a* and 399*b*, thereby heating the inside of the main chamber 390 to be maintained at a temperature higher than room temperature, or cooling the inside of the main chamber 390 to be maintained at a temperature lower than room temperature, or maintaining the inside of the main chamber 390 at a constant temperature nearly equal to room temperature. In the main chamber 390, a temperature sensor 400 for monitoring the temperature inside the main chamber 390 is provided. The temperature sensor 400 may be provided inside the temperature adjustment chamber 392.

Regarding the convection generating means 399*a* and 399*b*, in the present embodiment, the convection generating means 399*a* located near the temperature adjusting means 398 causes the convection that flows into the temperature adjustment chamber 392 from the through-hole 397*a* located above the convection generating means 399*a*, to flow in the horizontal direction in the temperature adjustment chamber 392, thereby transmitting the cold or hot air generated from the temperature adjusting means 398 to the through-hole 397*b* located distant from the temperature adjusting means 398. The convection generating means 399*b* is located beneath the through-hole 397*b*, and converts the horizontal air current generated by the convection generating means 399*a* into upward air current heading toward the through-hole 397*b* located above. Thus, the cold or hot air generated from the temperature adjusting means 398 can be efficiently transmitted from the through-hole 397*b* into the main chamber 390.

In the present embodiment, a duct 401 is provided to the rear of the temperature adjustment chamber 392. The duct 401 discharges cold exhaust heat or hot exhaust heat generated by the temperature adjusting means 398 to the outside of the sample preparation section 8. The duct 401 is provided with: a fan 402 which causes the cold exhaust heat or the hot exhaust heat to flow to the rear side; and an exhaust port 403 through which the air current generated by the fan 402 is discharged to the outside of the duct 401. The duct 401 is disposed beneath an external processing unit 37.

Figure 8:
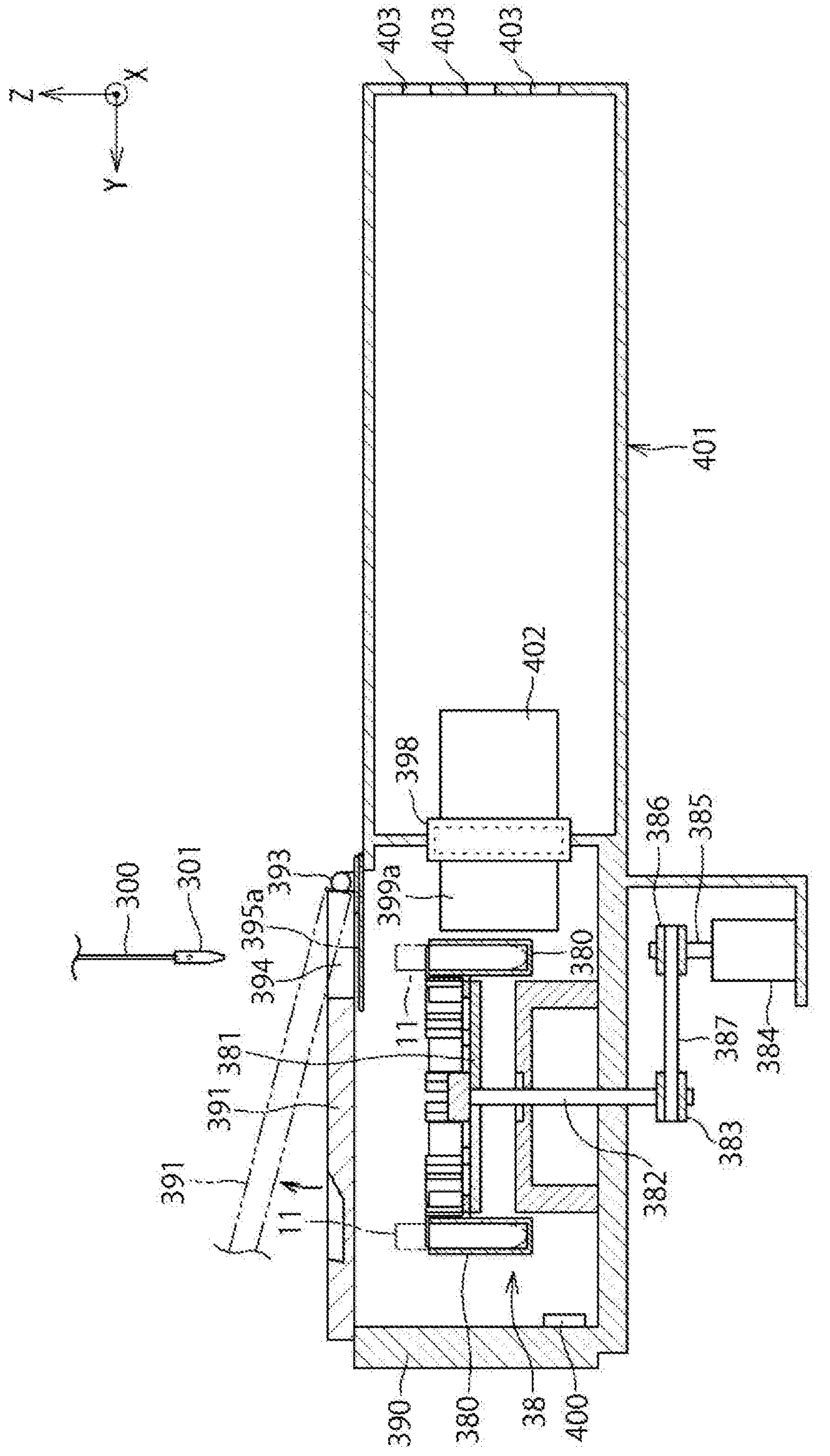
FIG. 8 is a cross-sectional view of a modification of the sample preparation section.

As shown in FIG. 8, the temperature adjustment chamber 392 is not necessarily provided. In this case, the temperature adjusting means 398 is provided in the main chamber 390, preferably, at the rear side in the main chamber 390, and the duct 401 is provided to the rear of the main chamber 390. The convection generating means 399*a* is disposed near the temperature adjusting means 398 so as to cause horizontal air current in the main chamber 390.

The sample preparation section 3 may be provided with the external processing unit 60, in addition to the above-described components. The external processing unit 60 is not subjected to temperature adjustment, and is used for performing processing at room temperature. In the present embodiment, the external processing unit 60 is provided with: a disposal unit 600 into which supernatant in the dispensing tube 11 is discarded; and an agitation unit 601 which agitates the liquid in the dispensing tube 11. In the disposal unit 600, the supernatant in the dispensing tube 11 is discarded by decanting, that is, by inclining the dispensing tube 11 held by the gripper 360 by using the movement means 361, or by aspirating the supernatant by using the nozzles 300 of the dispensers 30A and 30B. The agitation unit 601 is implemented by, for example, a vortex mixer that shakes and agitates the liquid in the dispensing tube 11 held by the gripper 360. The external processing unit 60 may be configured to perform, at room temperature, processing other than discarding of the supernatant in the dispensing tube 11 and agitation of the liquid in the dispensing tube 11.

Structure of Control Section

As shown in FIG. 1, the control section 4 includes: a processor 40; a memory 41 used for reading a control program stored in a storage unit 42, and used as a work area for data processing of the processor 40; and the storage unit 42 which stores therein various control programs and various data with which the processor 40 performs operation control for the respective components such as the measurement section 2 and the sample preparation section 3. The memory 41 is implemented by a RAM (random access memory). The storage unit 42 is implemented by a ROM (read only memory), a hard disk, or the like.

The control section 4 obtains, for example, detection signals outputted from the light receiving elements 22A to 22F of the measurement section 2 via the signal processing section 6, and stores the detection signals in the storage unit 42.

The control section 4 controls operations of the nozzles 300 and the nozzle transfer means 302 of the specimen dispenser 30A and the reagent dispenser 30B in the sample preparation section 3, to cause the nozzles 300 to move and perform aspiration and discharge of liquid such as a reagent.

The control section 4 controls operations of the temperature adjusting means 310 of the specimen container setting unit 31 and the temperature adjusting means (not shown) of the reagent setting unit 35 in the sample preparation section 3 on the basis of a detection signal from the temperature sensor (not shown), to perform temperature adjustment for the specimen container setting unit 31 and the reagent setting unit 35.

The control section 4 controls operation of the tube transfer unit 36 in the sample preparation section 3 to transfer and hold the dispensing tube 11.

The control section 4 controls the opening/closing means 395 in the sample preparation section 3 to open and close the entrance ports 394 and 396.

The control section 4 controls the centrifuge 38 in the sample preparation section 3 to perform centrifugation.

The control section 4 controls the temperature adjusting means 398 and the convection generating means 399*a* and 399*b* in the sample preparation section 3 on the basis of a detection signal from the temperature sensor 400, to perform temperature adjustment for the centrifuge 38.

The control section 4 controls operation of the fan 402 of the sample preparation section 3 to discharge cold heat and hot heat from the centrifuge 38.

The control section 4 obtains a detection signal from the liquid level detecting sensor serving as the liquid amount detecting means 37 in the sample preparation section 3, and stores the detection signal in the storage unit 42.

The control section 4 obtains identification information (IDs) of the respective reagents (the cell detection reagent and the reagents other than the cell detection reagents) read by the reception unit 39 of the reagent setting unit 35 in the sample preparation section 3. Then, on the basis of the identification information (IDs) of the respective reagents that have been read, the control section 4 stores, in the storage unit 42, data indicating which reagents are set in which positions in the reagent setting unit 35. In addition, on the basis of the identification information (IDs) of the respective cell detection reagents that have been read, the control section 4 reads information relating to preparation of measurement samples corresponding to a test item to be tested by using the respective cell detection reagents corresponding to the identification information (IDs) stored in the storage unit 42. Then, on the basis of the information relating to preparation of measurement samples, the control section 4 controls the sample preparation section 3 to perform a concentration adjustment process for measurement target particles in the specimen, and a measurement sample preparation process. The information relating to preparation of measurement samples is uniquely determined by the user in accordance with the specimen to be measured, and is stored in a file called a work list together with the types of the cell detection reagents, etc.

The manner of preparing measurement samples varies depending on measurement items (e.g., whether or not to analyze the amount of DNA, what type of antigen is used, etc.). Therefore, for each measurement item, a measurement sample suitable for cell analysis for the measurement item needs to be prepared. Information relating to preparation of measurement samples includes information relating to preparation of measurement samples corresponding to measurement items for measurement target cells. Therefore, by preparing measurement samples on the basis of the information relating to preparation of measurement samples, it is possible to prepare measurement samples suitable for analysis of measurement target cells.

The information relating to preparation of measurement samples may include information such as: information of measurement items that can be measured, and information of a test item; properties of cell detection reagents used for cell analysis (including information of measurement items, information of labeling substances by which antibody and the like are labeled, cross-reactivity of antibody, measurement items that can be simultaneously measured, etc.); the type of specimen; the number of cells necessary for performing cell analysis by using each cell detection reagent (necessary number of cells); the ratio of measurement target cells contained in a predetermined amount of specimen; the amount of specimen; the types of other reagents necessary for preparation of measurement samples; the dispensing amount of each reagent; the order of reagents to be dispensed; temperature during dispensing of each reagent; and the number of measurement samples (dispensing tubes 11) necessary for measurement.

The control section 4 is connected to the analysis section 5 via a communication interface 7, and transmits/receives data measured by the measurement section 2 and data necessary for processes in the respective components to/from the analysis section 5.

Structure of Analyzer

Figure 9:
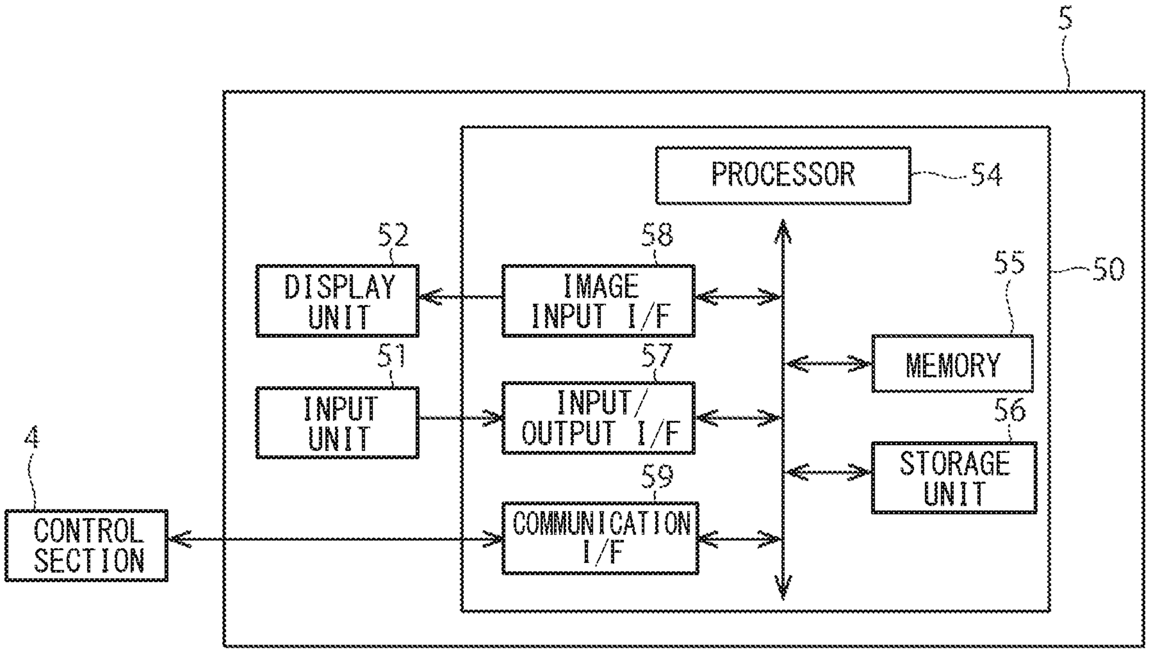
FIG. 9 is a block diagram of an analyzer.

As shown in FIG. 9, the analysis section 5 includes a processing unit 50, an input unit 51, and a display unit 52. The processing unit 50 includes a processor 54, a memory 55, a storage unit 56, an input/output interface 57, an image output interface 58, and a communication interface 59. The processing unit 50 can be implemented by a general-purpose computer. The memory 55 is implemented by a RAM (random access memory). The memory 55 is used for reading a computer program stored in the storage unit 56. In addition, the memory 55 is used as a work area for various kinds of data processing of the processor 54. The storage unit 56 is implemented by a ROM (read only memory), a hard disk, or the like. The storage unit 56 stores therein computer programs and various kinds of processing data used therefor. The storage unit 56 (e.g., hard disk) has, stored therein, operation programs for performing: transmission of operation instructions to the control section 4; reception and analysis processing of measurement data obtained in the measurement section 2; and display of processed analysis results.

The input unit 51 is implemented by, for example, a touch panel, a key board, a mouse, a pen tablet, or the like. The display unit 52 is implemented by, for example, a display or the like.

Operation of Control Section

Figure 10:
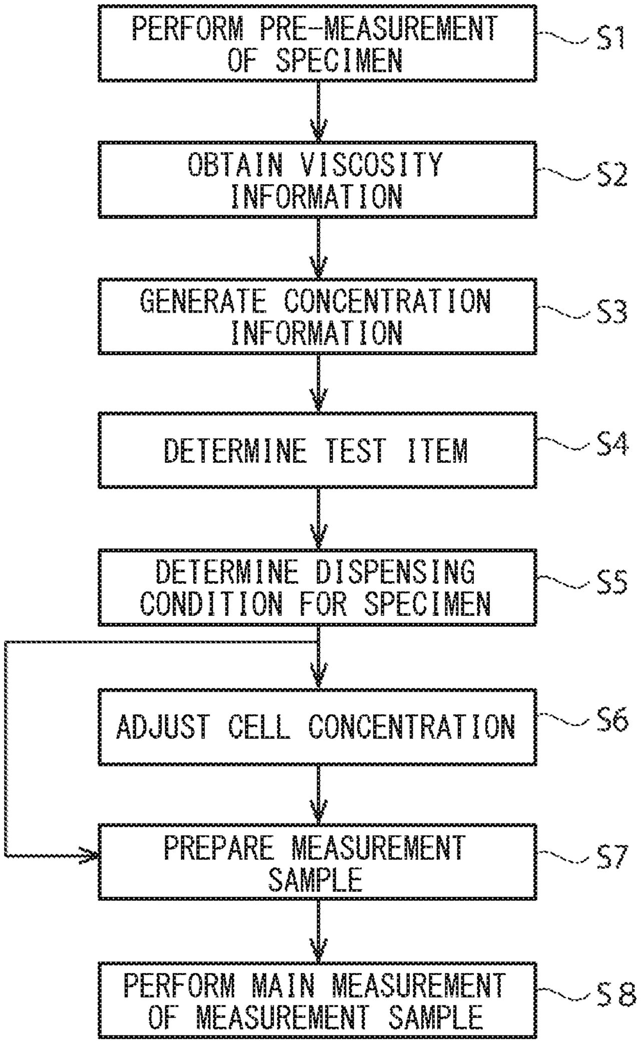
FIG. 10 is a flowchart showing an outline of an operation procedure of processing of a control section.

As shown in FIG. 10, the control section 4 performs processes in the following steps: pre-measurement step S1 of measuring a specimen obtained from a specimen container 10; an obtainment step S2 of obtaining viscosity information relating to the viscosity of the specimen on the basis of measurement data obtained in the pre-measurement step; generation step S3 of generating concentration information of measurement target cells in the specimen contained in the specimen container 10, from measurement target cells of the specimen detected, on the basis of the measurement data obtained in the pre-measurement step; determination step S4 of determining a test item upon obtaining information about types of particle detection reagents used for preparation of measurement samples; determination step S5 of determining, on the basis of the obtained viscosity information, a specimen dispensing condition (at least one of an aspiration condition for aspirating the specimen and a discharge condition for discharging the specimen); an adjustment step S6 of automatically adjusting the concentration of the measurement target cells in the specimen, in accordance with the generated concentration information, and the types of the cell detection reagents used for preparation of measurement samples (information relating to preparation of measurement samples); preparation step S7 of preparing measurement samples from the specimen and the cell detection reagents; and main measurement step S8 of performing measurement of the measurement samples. Hereinafter, operation of the control section 4 will be described in detail.

First Example

A first example of operation of the control section 4 will be described with reference to FIG. 11 and FIG. 12A. A flow described below is merely an example, and the operation of the control section 4 is not limited to the flow. The first example is an example in which a plurality of cell detection reagents necessary for preparation of a measurement sample to be used for measuring respective measurement items corresponding to a predetermined test item are all mixed with a specimen in a single dispensing tube 11, thereby preparing the measurement sample.

Figure 11:
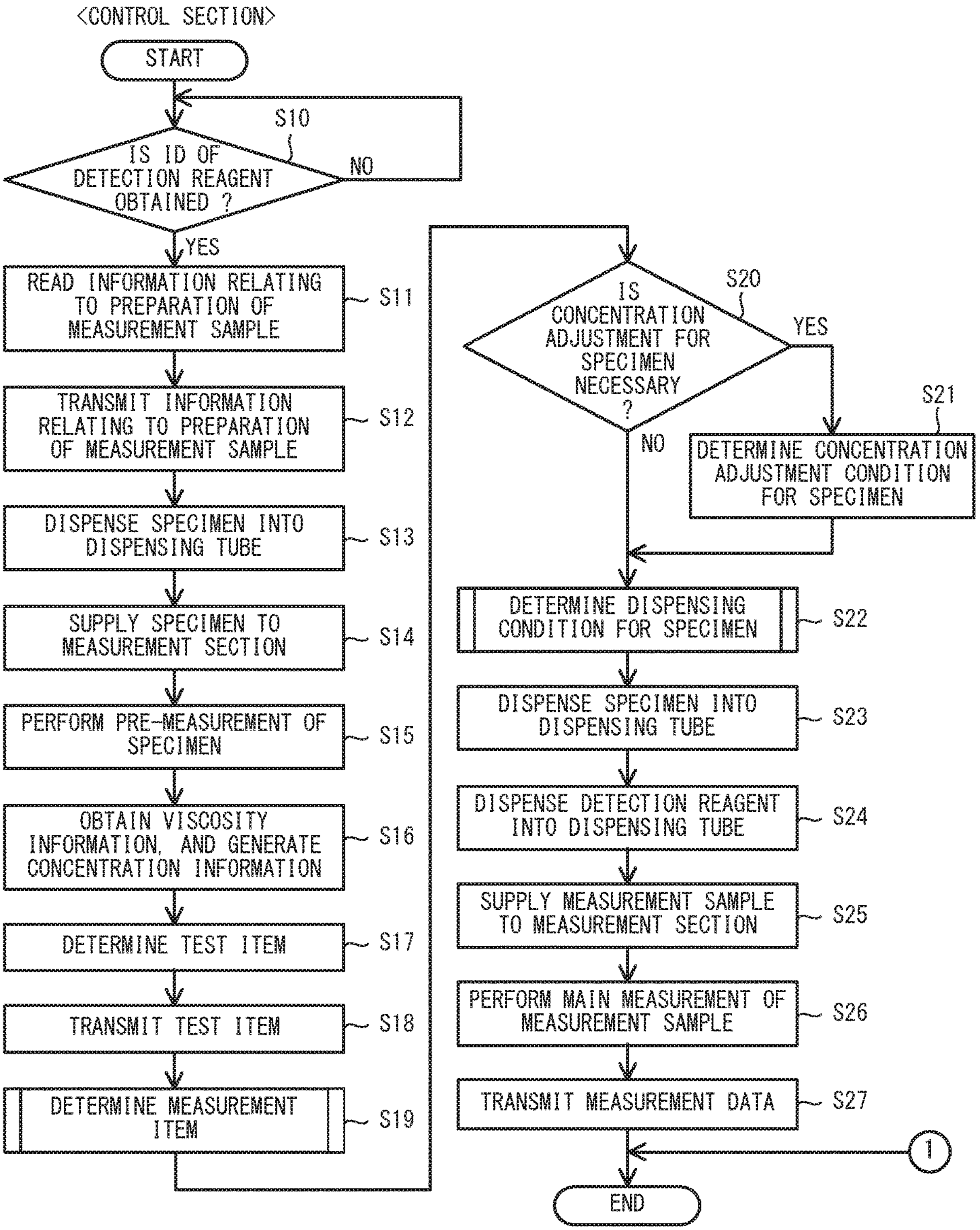
FIG. 11 is a flowchart showing the operation procedure of the processing of the control section.
Figure 12A:
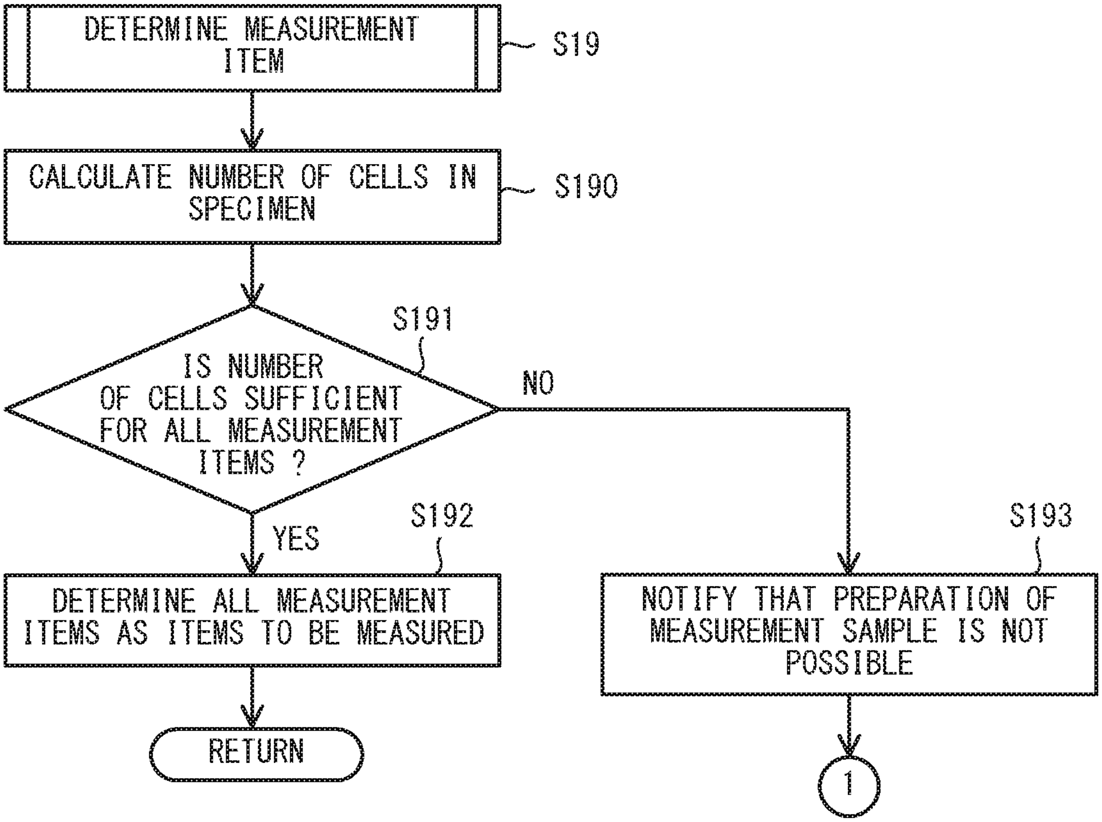
FIG. 12A is a flowchart showing an operation procedure of a first example of processing in S19 in FIG. 11.

First, in S10 in FIG. 11, the control section 4 receives input of identification information (IDs) of cell detection reagents to be used for preparation of a measurement sample. In advance of measurement, a plurality of cell detection reagents and reagents other than the cell detection reagents, which are necessary for preparation of the measurement sample, have been set in the reagent setting unit 35 of the sample preparation section 3. At this time, the reception unit 39 of the reagent setting unit 35 obtains the identification information (IDs) of the reagents in the reagent containers 350 from barcodes or the like attached to the reagent containers 350. Upon receiving the identification information (IDs) of the respective reagents, the control section 4 determines the types of particle detection reagents to be used for preparation of the measurement sample on the basis of the identification information (IDs), and proceeds to S11. In S11, the control section 4 reads, from the storage unit 42, information relating to preparation of a measurement sample for respective measurement items corresponding to a test item to be tested by using the determined types of cell detection reagents. In addition, in S12, the control section 4 transmits the read information relating to preparation of the measurement sample to the analysis section 5. Further, the control section 4 stores, in the storage unit 42, data indicating which reagents are set in which positions in the reagent setting unit 35.

For example, FIG. 13A shows an example of information relating to preparation of a measurement sample, stored in the storage unit 42, in an exemplary case in which the specimen is peripheral blood, and the test item is regulatory T cells. In FIG. 13A, CD25, and CD3 and CD4 denote cell surface markers, and cell detection reagents 2 and 3 contain antibodies that bind to these cell surface markers, respectively. The antibodies are labeled with fluorescent substances shown in FIG. 13A. FoxP3 is an intranuclear protein, and a cell detection reagent 4 contains a fluorescence-labeled anti-FoxP3 antibody against the protein. The information relating to preparation of the measurement sample shown in FIG. 13A further includes information such as: the necessary number of cells (white blood cells) required for performing cell analysis by using each of the cell detection reagents 1 to 4; the amount of specimen; the types of other reagents necessary for preparation of the measurement sample; the mixing amount of each reagent; the order of reagents to be dispensed; etc.

Next, in S13, the control section 4 controls the specimen dispenser 30A in accordance with dispensing conditions described later, and causes the nozzle 300 to aspirate a portion of the specimen in the specimen container 10 set in the specimen container setting unit 31, and discharge the specimen into the dispensing tube 11. The specimen may be discharged into the dispensing tube 11 set in the dispensing tube setting unit 32, or may be discharged into the dispensing tube 11 set in the centrifuge 38 by using the tube transfer unit 36. According to need, a predetermined amount of a diluent set in the reagent setting unit 35 may be aspirated by the nozzle 300 of the reagent dispenser 30B, and discharged into the dispensing tube 11 in which the specimen has been dispensed, so that the diluent is mixed with the specimen. Further, the control section 4 calculates the liquid amount of the specimen in the specimen container 10 on the basis of a detection signal from a liquid level detecting sensor (not shown) serving as the liquid amount detecting means 37. Further, according to need, the control section 4 controls the intra-nozzle liquid amount detecting means 30A1 or the dispensed liquid amount detecting means to monitor the liquid amount of the dispensed specimen.

Next, in S14, the control section 4 controls the tube transfer unit 36 to transfer the dispensing tube 11 in which the specimen has been dispensed, to the measurement section 2. When the dispensing tube 11 has been transferred to a predetermined position 29 (shown in FIG. 3) in the measurement section 2, the specimen is aspirated from the dispensing tube 11 by an aspirator 29*a* capable of raising/lowering operation in the vertical direction (Z direction), and is supplied to the measurement section 2. Thus, in S15, the control section 4 controls the measurement section 2 to perform, by using the first measurement section 2*a*, measurement of the specimen on the basis of electric resistance. Then, in S16, the control section 4 obtains viscosity information in each specimen, such as a hematocrit value (%), the number of red blood cells per unit volume, a mean corpuscular volume, the number of platelets per unit volume, or the like.

In S15, the control section 4 controls the measurement section 2 to perform, by using the second measurement section 2*b*, measurement of the specimen on the basis of flow cytometry analysis, thereby counting the number of measurement target cells in the specimen. Then, in S16, the control section 4 generates concentration information of the measurement target cells in the specimen contained in the specimen container 10, on the basis of measurement data obtained by the second measurement section 2*b*. The concentration of the measurement target cells in the specimen means the number of the measurement target cells per unit volume of the specimen. Specifically, the amount of the specimen aspirated from the specimen container 10 by the nozzle 300 of the specimen dispenser 30A for the purpose of measuring the specimen can be obtained from the flow rate sensor (not shown) provided in the specimen dispenser 30A. By dividing the number of measurement target cells (measurement data) counted by the second measurement section 2*b* by the amount of the aspirated specimen, concentration information of the measurement target cells in the specimen can be generated.

When the second measurement section 2*b* is a flow cytometer, the number of measurement target cells can be counted on the basis of a detection signal of forward scattered light. Further, when the second measurement section 2*b* is a flow cytometer, the number of measurement target cells can be counted in consideration of the ratio of the measurement target cells to a plurality of types of cells contained in the specimen. Specifically, the number of all cells counted by the second measurement section 2*b* is multiplied by the ratio of the measurement target cells also counted by the second measurement section 2*b*, whereby the number of measurement target cells and the concentration of the measurement target cells can be calculated.

Next, in S17, the control section 4 determines a test item. Determination of a test item is performed by, on the basis of the identification information (IDs) of the plurality of cell detection reagents obtained by the reception unit 39, specifying a test item including the identification information (IDs) of the respective cell detection reagents. For example, in the example shown in FIG. 13A, on the basis of the identification information (IDs) 1 to 4 of the cell detection reagents obtained by the reception unit 39, a test item A (regulatory T cells) is determined. In S18, the control section 4 transmits the determined test item to the analysis section 5.

The control section 4 compares the concentration information of the measurement target cells in the specimen, which has been generated in S16, with a reference value stored in the storage unit 42, and then if the concentration of the measurement target cells is higher than the reference value, the control section 4 may measure a test item corresponding to other cell detection reagents set in the reagent setting unit 35.

For example, when the specimen is peripheral blood, the control section 4 compares the concentration information of the measurement target cells (preferably, nucleated cells) obtained in the pre-measurement, with a reference value of the number of cells, stored in the storage unit 42. This reference value is about 15,000/μl when the specimen is peripheral blood, for example. When the concentration of the nucleated cells obtained in the pre-measurement exceeds this value, hematologic malignancy is suspected. Therefore, upon determining that the concentration of the nucleated cells obtained in the pre-measurement exceeds the value, the control section 4 controls the sample preparation section 3 to prepare a measurement sample for adding an analysis item for identifying hematologic malignancy. The analysis item for identifying hematologic malignancy may be protein or nucleic acid.

Next, in S19, the control section 4 determines whether or not all the measurement items can be measured. In S19, first, in S190 in FIG. 12A, the number of measurement target cells (total number of cells) in the specimen contained in the specimen container 10 is calculated on the basis of the concentration information of the measurement target cells in the specimen, which has been generated in S16, and the amount of the specimen in the specimen container 10. Next, in S191, the control section 4 determines whether or not the calculated number of measurement target cells in the specimen is equal to or larger than the number of cells sufficient for measurement of all the measurement items for the test item.

Figure 14:
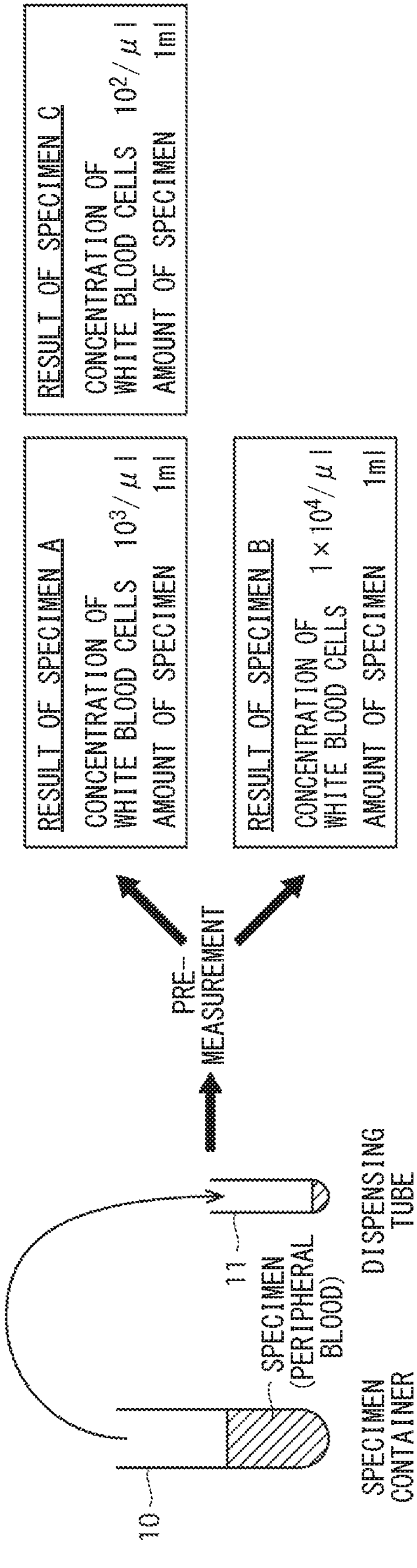
FIG. 14 is a diagram showing an example of measurement data obtained by detecting measurement target particles in a specimen by measuring the specimen contained in a specimen container.

For example, in the example shown in FIG. 13A, the number of white blood cells necessary for measurement of regulatory T cells is, for example, $1\times10^4$. As shown in FIG. 14, when the white blood cell concentration in a specimen A is $1\times10^3$/μl and the amount of the specimen is 1 ml according to the result of the pre-measurement for specimens, the number of white blood cells that are measurement target cells in the specimen A is $1\times10^6$. Therefore, the specimen A satisfies the measurement conditions for all the measurement items. Meanwhile, since the number of white blood cells that are measurement target cells in a specimen B is $1\times10^7$ and $1\times10^5$, respectively, the specimens B and C also satisfy the measurement conditions for all the measurement items. Therefore, in this case, the result in S191 in FIG. 12A is "YES", and the control section 4 proceeds to S192, and determines that all the measurement items are items to be measured. Further, the control section 4 stores the determination result in the storage unit 42, transmits the determination result to the analysis section 5, and proceeds to S20 in FIG. 11.

Meanwhile, although not shown, when the number of white blood cells that are measurement target cells in the specimen is less than $1\times10^4$, a measurement condition for a measurement item using the cell detection reagent 4 is not satisfied. In this case, the result in S191 is "NO", and the processing proceeds to S193. In S193, the control section 4 transmits, to the analysis section 5, a notification that the necessary number of cells for performing measurement of the measurement item is not secured and therefore the measurement item cannot be measured.

If addition of specimen can make the number of measurement target cells in the specimen equal to or larger than the number of cells sufficient for measurement of all the measurement items, the specimen may be condensed by the centrifuge 38 and new specimen may be mixed, thereby making the number of measurement target cells in the specimen equal to or larger than the number of cells sufficient for measurement of all the measurement items.

Next, in S20 in FIG. 11, the control section 4 determines whether or not concentration adjustment for the specimen is needed. Whether or not concentration adjustment for the specimen is needed is determined on the basis of the concentration information of the measurement target cells in the specimen, which has been generated in S16, and the particle detection reagents used for preparation of the measurement sample. When the concentration of the measurement target cells in the specimen is higher than a predetermined value or lower than the predetermined value, it is determined that concentration adjustment is needed. On the other hand, when the concentration of the measurement target cells in the specimen has the predetermined value, it is determined that concentration adjustment is not needed. The predetermined value may be a fixed value, or may have a fixed range.

For example, in the example shown in FIG. 13A, since the number of white blood cells necessary for measurement of regulatory T cells is $1\times10^4$ and the amount of specimen is 10 μl, the concentration of white blood cells that are measurement target cells in the specimen, which is the above-described predetermined value, is $1\times10^3$/μl. As shown in FIG. 14, according to the result of the pre-measurement for specimens, the concentration of white blood cells of the specimen A is $1\times10^3$/μl, the concentration of white blood cells of the specimen B is $1\times10^4$/μl, and the concentration of white blood cells of a specimen C is $1\times10^2$/μl. In this case, since the concentration of white blood cells in the specimen A has the predetermined value, it is determined that concentration adjustment is not needed for the specimen A. Meanwhile, since the concentration of white blood cells in the specimen B is higher than the predetermined value and the concentration of white blood cells in the specimen C is lower than the predetermined value, it is determined that concentration adjustment is needed for specimens B and C.

For some measurement items, the ratio of measurement target cells in the specimen may be low. For example, hematopoietic stem cells (measurement target cells) in bone marrow corresponds to this case. In this case, whether or not condensed preparation of the specimen is needed is determined on the basis of information about the ratio of measurement target cells per unit amount of the specimen, contained in the cell detection reagent. Condensed preparation of the specimen in this case may be performed by centrifugation described later. When the flow cytometer is provided with a sorting function, the measurement target cells may be recovered from the specimen and condensed by using the sorting function.

Upon determining in S20 in FIG. 11 that concentration adjustment for the specimen is not needed, the control section 4 proceeds to S22, and determines a dispensing condition for the specimen on the basis of viscosity information of the specimen. Then, in S23, the control section 4 controls the specimen dispenser 30A on the basis of the determined dispensing condition, to cause the nozzle 300 to aspirate a predetermined amount of the specimen and discharge the specimen into the dispensing tube 11. Determination of the dispensing condition for the specimen in S22 will be described later in detail.

Next, the control section 4 controls the tube transfer unit 36 to set the dispensing tube 11 in which the specimen has been dispensed, in the centrifuge 38 in the sample preparation section 3. Thereafter, in S24, on the basis of the information relating to preparation of the measurement sample, the control section 4 controls the reagent dispenser 30B to dispense, into the dispensing tube 11, the cell detection reagents and the reagents other than the cell detection reagents for the purpose of preparing the measurement sample.

Specifically, the control section 4 controls the measurement sample preparation operation (dispensing, dilution, washing, etc.) of the sample preparation section 3, on the basis of: the types of the cell detection reagents necessary for preparation of the measurement sample; the types of the reagents other than the cell detection reagents, necessary for preparation of the measurement sample; the order of the reagents to be dispensed; the dispensing amount of each reagent; the amount of the specimen; etc., which are included in the information relating to preparation of the measurement sample. In preparing the measurement sample, according to need, the control section 4 may control the centrifuge 38 to perform centrifugation, and may control the reagent dispenser 30B to remove supernatant in the dispensing tube 11. Further, information relating to temperature at dispensing of each reagent may be included in the information relating to preparation of the measurement sample. The control section 4 may control the temperature adjusting means 398 and the convection generating means 399*a* and 399*b* to adjust the temperature in the centrifuge 38 when each reagent is dispensed, on the basis of the information relating to the temperature at dispensing of each reagent, which is included in the information relating to preparation of the measurement sample.

Figures 15A, 15B, 15C:
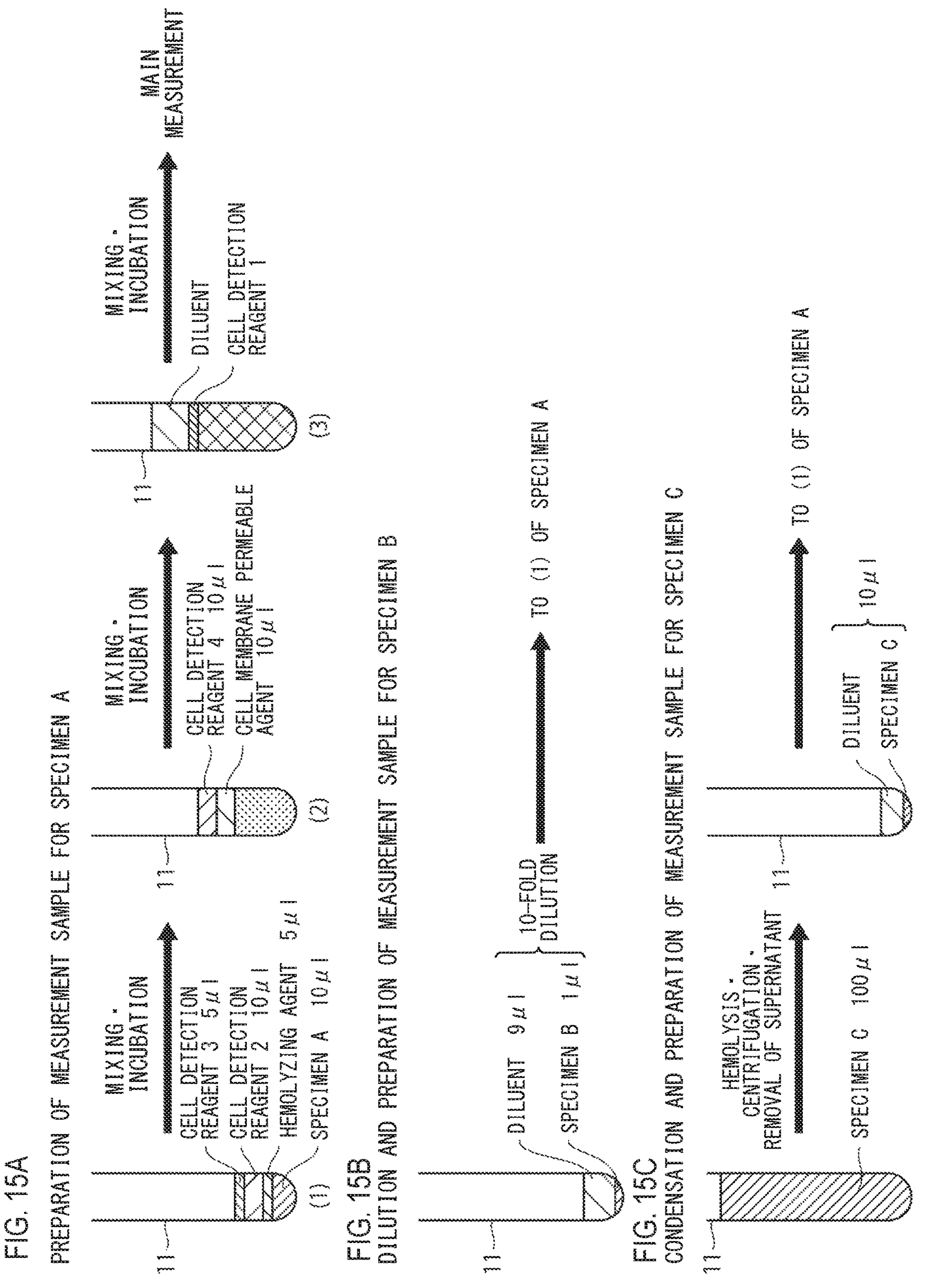
FIGS. 15A through 15C are diagrams showing examples of measurement sample preparation methods with respect to specimens A to C.

For example, the above operation will be described taking the specimen A shown in FIG. 14 as an example. As shown in FIG. 15A, the control section 4 controls the specimen dispenser 30A to dispense a portion of the specimen A from the specimen container 10 into a dispensing tube 11 other than that used for the pre-measurement. Regarding the amount of specimen to be dispensed into the dispensing tube 11, since the number of white blood cells necessary for measurement of regulatory T cells is $1\times10^4$ as shown in FIG. 13A and the concentration of white blood cells in the specimen A is $10^3$/μl, the necessary number of cells is satisfied when 10 μl of specimen A is dispensed into the dispensing tube 11 for preparing the measurement sample.

Next, the control section 4 controls the tube transfer unit 36 to transfer the dispensing tube 11 containing the specimen A to the centrifuge 38 in the sample preparation section 3, and set the dispensing tube 11 therein. In a case where regulatory T cells are analyzed by using peripheral blood as a specimen, in accordance with the information relating to preparation of the measurement sample shown in FIG. 13A, since it is desirable to hemolyze red blood cells first, the control section 4 controls the reagent dispenser 30B to dispense 5 μl of hemolyzing agent set in the reagent setting unit 35 into the dispensing tube 11 containing the specimen A. Subsequently, according to the information relating to preparation of the measurement sample shown in FIG. 13A, the control section 4 controls the reagent dispenser 30B to dispense 10 μl of the cell detection reagent 2 and 5 μl of the cell detection reagent 3, which are set in the reagent setting unit 35, into the dispensing tube 11 containing the specimen. Subsequently, the control section 4 controls the reagent dispenser 30B to dispense 10 μl of the cell membrane permeable agent set in the reagent setting unit 35, into the dispensing tube 11 containing the cells reacted with the cell detection reagent 2 and the cell detection reagent 3. Subsequently, the control section 4 controls the reagent dispenser 30B to dispense 10 μl of the cell detection reagent 4 set in the reagent setting unit 35, into the dispensing tube 11 in which 10 μl of the cell membrane permeable agent has been mixed. Finally, the control section 4 controls the reagent dispenser 30B to dispense 5 μl of the cell detection reagent 1 set in the reagent setting unit 35, into the dispensing tube 11 in which the cell detection reagent 4 has been mixed. The cell detection reagent 1 is a nucleus stain.

In the example shown in FIG. 15A, after each cell detection reagent has been dispensed, incubation is preferably performed for about 15 to 30 minutes to cause a sufficient reaction between the cells and the antibody. After the incubation and before dispensing of the next cell detection reagent, the cells may be washed. The manner of washing is not limited. For example, washing may be performed by centrifuging the dispensing tube 11 containing the cells by the centrifuge 38, removing supernatant, and adding a diluent or the like to resuspend the cells.

Then, in S25, the control section 4 controls the tube transfer unit 36 to transfer the dispensing tube 11 containing the measurement sample prepared as described above, to the measurement section 2. When the dispensing tube 11 has been transferred to the predetermined position 29 (shown in FIG. 3) in the measurement section 2, the measurement sample is aspirated from the dispensing tube 11 by the aspirator 29*a* capable of raising/lowering operation in the vertical direction (Z direction), and is supplied to the flow cell 20 in the second measurement section 2*b*. Thus, in S26, the control section 4 causes the second measurement section 2*b* to perform main measurement of the measurement sample according to the flow cytometry method.

Meanwhile, upon determining in S20 that concentration adjustment for the specimen is needed, the control section 4 proceeds to S21, and determines a concentration adjustment condition for the specimen in the specimen container 10. Specifically, when the concentration of the measurement target cells in the specimen is higher than the predetermined value, the control section 4 performs dilution of the specimen under a predetermined condition for the purpose of making the concentration of the measurement target cells in the specimen equal to the predetermined value. When the concentration of the measurement target cells in the specimen is smaller than the predetermined value, the control section 4 performs condensation of the specimen under a predetermined condition for the purpose of making the concentration of the measurement target cells in the specimen equal to the predetermined value. Further, in S22, the control section 4 determines a dispensing condition for the specimen on the basis of the viscosity information of the specimen. Then, in S23, the control section 4 controls the specimen dispenser 30A on the basis of the determined dispensing condition, to cause the nozzle 300 to aspirate a predetermined amount of the specimen and discharge the specimen into the dispensing tube 11.

For example, the above operation in the case where the concentration of the measurement target cells in the specimen is higher than the predetermined value will be described taking the specimen B shown in FIG. 14 as an example. As shown in FIG. 15B, the control section 4 controls the specimen dispenser 30A to dispense a portion of the specimen B from the specimen container 10 into a dispensing tube 11 other than that used for the pre-measurement. Regarding the amount of the specimen to be dispensed into the dispensing tube 11, since the number of white blood cells necessary for measurement of regulatory T cells is $1\times10^4$ as shown in FIG. 13A and the concentration of white blood cells in the specimen B is $1\times10^4$/μl, the necessary number of cells is satisfied when 1 μl of the specimen B is dispensed into the dispensing tube 11 for preparing the measurement sample. Since the concentration of white blood cells in the specimen B is 10 times as dense as the predetermined value of $1\times10^3$/μl, the specimen B is diluted at a rate of 10 fold by the diluent so that the amount of the specimen becomes 10 μl, thereby making the concentration of white blood cells equal to the predetermined value.

When the concentration of the measurement target cells in the specimen is lower than the predetermined value, the specimen is condensed. Condensation of the specimen can be performed by centrifugation by the centrifuge 38, for example.

The above operation will be described taking the specimen C shown in FIG. 14 as an example. As shown in FIG. 15C, the control section 4 controls the specimen dispenser 30A to dispense a portion of the specimen C from the specimen container 10 into a dispensing tube 11 other than that used for the pre-measurement. Regarding the amount of the specimen to be dispensed into the dispensing tube 11, since the number of white blood cells necessary for measurement of regulatory T cells is $1\times10^4$ as shown in FIG. 13A and the concentration of white blood cells in the specimen C is $1\times10^2$/μl, the necessary number of cells is satisfied when 100 μl of the specimen B is dispensed into the dispensing tube 11 for preparing the measurement sample. Then, the control section 4 controls the centrifuge 38 to centrifuge the specimen C, and controls the reagent dispenser 30B to aspirate and remove supernatant from the dispensing tube 11 and to mix the diluent so that the amount of the specimen becomes 10 μl, whereby the concentration of white blood cells can be made equal to the predetermined value. In this case, condensation of the specimen is preferably performed after the red blood cells are dissolved.

After the concentration adjustment for the specimen is finished, the control section 4 proceeds to S24 in FIG. 11. In S24, the control section 4 controls the reagent dispenser 30B on the basis of the information relating to preparation of the measurement sample, thereby preparing the measurement sample by, for example, dispensing the cell detection reagents and the reagents other than the cell detection reagents into the dispensing tube 11. Then, in S25, the control section 4 controls the tube transfer unit 36 to transfer the dispensing tube 11 containing the prepared measurement sample, to the measurement section 2. In S26, the control section 4 performs main measurement of the measurement sample according to the flow cytometry method by using the second measurement section 2*b*.

Then, in S27, the control section 4 transmits measurement data of the main measurement from the measurement section 2 to the analysis section 5. The processing unit 50 in the analysis section 5 analyzes the specimen by using the measurement data of the main measurement, and determines whether or not abnormality occurs in the measurement target cells in the specimen.

Second Example

Figure 12B:
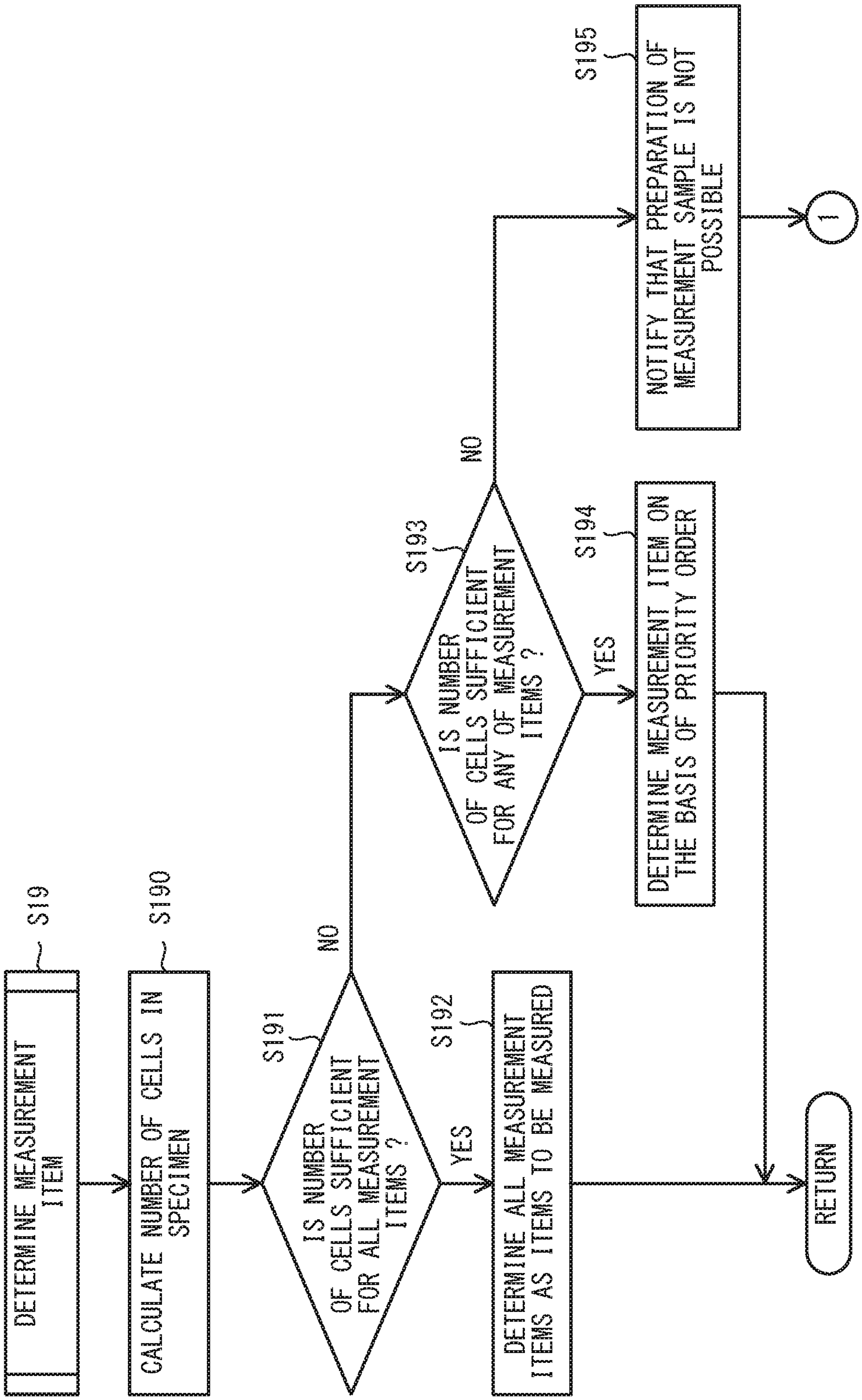
FIG. 12B is a flowchart showing an operation procedure of a second example of processing in S19 in FIG. 11.

A second example of operation of the control section 4 will be described with reference to FIG. 11 and FIG. 12B. A flow described below is merely an example, and the operation of the control section 4 is not limited to the flow. The second example is an example in which measurement samples for measuring respective measurement items for a predetermined test item are prepared in different dispensing tubes 11. FIG. 13B shows an example of information relating to preparation of measurement samples, which is stored in the storage unit 42 of the control section 4 according to the second example. In this second embodiment, an operation in a case where, as cell detection reagents, cell detection reagents 2 to 5 are respectively mixed with a specimen in different dispensing tubes 11 to prepare four types of measurement samples (measurement samples 1 to 4), will be described. An operation in a case where a plurality of measurement samples other than three types are prepared is similar to the operation described below.

Since S10 to S18 in FIG. 11 are the same as those of the first example, detailed description thereof is omitted.

Next, in S19, the control section determines measurement items. In S19, first, in S190 in FIG. 12B, the number of measurement target cells (total number of cells) in the specimen contained in the specimen container 10 is calculated on the basis of the concentration information of the measurement target cells in the specimen, which has been generated in S16, and the amount of the specimen in the specimen container 10. Next, in S191, the control section 4 determines whether or not the calculated number of measurement target cells in the specimen is equal to or larger than the number of cells sufficient for measurement of all the measurement items for the test item. The number of cells necessary for measurement of the measurement items can be obtained from the information relating to preparation of measurement samples.

For example, in the example shown in FIG. 13B, the number of white blood cells necessary for measurement of regulatory T cells is $17\times10^3$, because the number of white blood cells necessary for a measurement item using a cell detection reagent 2 is $5\times10^3$, the number of white blood cells necessary for a measurement item using a cell detection reagent 3 is $1\times10^3$, the number of white blood cells necessary for a measurement item using a cell detection reagent 4 is $1\times10^3$, and the number of white blood cells necessary for a measurement item using a cell detection reagent 5 is $10\times10^3$. As shown in FIG. 14, when the concentration of white blood cells in the specimen A is $1\times10^3/\mu l$ and the amount of the specimen is 1 ml according to the result of the pre-measurement of the specimen, the number of white blood cells that are measurement target cells in the specimen A is $1\times10^6$, and therefore, the specimen A satisfies the measurement conditions for all the measurement items. Meanwhile, since the number of white blood cells that are measurement target cells in the specimen B is $1\times10^7$ and $1\times10^5$, respectively, the specimens B and C also satisfy the measurement conditions for all the measurement items. Therefore, the result in S191 is “YES”, and the control section 4 proceeds to S192. In S192, the control section 4 determines that all the measurement items are items to be measured. Further, the control section 4 stores the determination result in the storage unit 42, and transmits the determination result to the analysis section 5, and then proceeds to S20 shown in FIG. 11.

Meanwhile, although not shown, when the number of white blood cells that are measurement target cells in the specimen is, for example, $16\times10^3$, the measurement conditions for all the measurement items are not satisfied. In this case, in S191, the control section 4 determines that the number of the measurement target cells in the specimen is not sufficient for measurement of all the measurement items, and proceeds to S193.

Next, in S193, the control section 4 determines whether or not the number of the measurement target cells in the specimen is equal to or larger than the number of cells sufficient for measurement of any of the measurement items for the test item. For example, in the example shown in FIG. 13B, when the number of white blood cells that are measurement target cells in the specimen is, for example, $16\times10^3$, the result in S193 is “YES”, and the control section 4 proceeds to S194. In S194, the control section 4 determines a measurement item to be measured, on the basis of the number of the measurement target cells in the specimen, and the priority order for the measurement items to be preferentially processed when the number of cells is insufficient, which is included in the information relating to preparation of measurement samples. That is, in descending order of the priorities of the measurement items, the control section 4 determines whether or not the number of cells that satisfies the measurement condition for each measurement item can be secured, and determines a measurement item, for which the number of cells that satisfies the measurement condition can be secured, as an item to be measured. The priority order for determining an item to be measured can be obtained from the information relating to preparation of measurement samples.

For example, in the example shown in FIG. 13B, when the number of white blood cells as measurement target cells in the specimen is $16\times10^3$, first, determination is performed on the measurement item using the cell detection reagent 5, which is assigned the first priority. Since the number of cells necessary for the first-priority measurement item is $10\times10^3$, the measurement condition for this measurement item is satisfied. Next, determination is performed on the measurement item using the cell detection reagent 2, which is assigned the second priority. Since the number of cells necessary for measurement of the second-priority measurement item is $5\times10^3$ and the remaining number of white blood cells that are measurement target cells in the specimen is $6\times10^3$, the measurement condition for this measurement item is satisfied. Next, determination is performed on the measurement item using the cell detection reagent 4, which is assigned the third priority. Since the number of cells necessary for measurement of the third-priority measurement item is $1\times10^3$ and the remaining number of white blood cells that are measurement target cells in the specimen is $1\times10^3$, the measurement condition for this measurement item is satisfied. Finally, determination is performed on the measurement item using the cell detection reagent 3, which is assigned the fourth priority. Since the number of cells necessary for measurement of the fourth-priority measurement item is $1\times10^3$ and the remaining number of white blood cells that are measurement target cells in the specimen is 0, the measurement condition for this measurement item is not satisfied. Therefore, in this case, the control section 4 determines that the measurement items using the cell detection reagents 2, 4, and 5 are items to be measured. Further, the control section 4 stores the determination result in the storage unit 42 and transmits the determination result to the analysis section 5, and the proceeds to S20 shown in FIG. 11.

On the other hand, upon determining in S193 that the number of the measurement target cells in the specimen is not sufficient for all the measurement items, the control section 4 proceeds to S195. In S195, the control section 4 transmits, to the analysis section 5, a notification that the number of cells necessary for performing measurement of the measurement items is not secured and therefore the measurement samples cannot be prepared.

Next, in S20 in FIG. 11, the control section 4 determines whether or not concentration adjustment for the specimen is needed. In this second example, for example, as shown in FIG. 13B, the respective measurement items have different concentrations of measurement target cells (white blood cells) in the specimen used for preparation of the measurement items. That is, a predetermined value of concentration of white blood cells in the specimen, which is required of the measurement item using the cell detection reagent 2, is $5\times10^2/\mu l$, a predetermined value of concentration of white blood cells in the specimen, which is required of the measurement item using the cell detection reagent 3, is $1\times10^2/\mu l$, a predetermined value of concentration of white blood cells in the specimen, which is required of the measurement item using the cell detection reagent 4, is $1\times10^2/\mu l$, and a predetermined value of concentration of white blood cells in the specimen, which is required of the measurement item using the cell detection reagent 5, is $1\times10^3/\mu l$. Therefore, for each of the measurement items, whether or not concentration adjustment is needed is determined on the basis of the concentration information of the measurement target cells in the specimen, which is generated in S16. When the concentration of the measurement target cells in the specimen is higher than the predetermined value or lower than the predetermined value, the control section 4 determines that concentration adjustment is needed, and proceeds to S21, S22, and S23 in order. Since the manner of determining a concentration adjustment condition in S21 is similar to that described for the first example, detailed description thereof is omitted. On the other hand, when the concentration of the measurement target cells in the specimen is equal to the predetermined value, the control section 4 determines the concentration adjustment is not needed, and proceeds to S22 and S23.

In S23, the control section 4 controls the specimen dispenser 30A to cause the nozzle 300 to aspirate a predetermined amount of the specimen for each measurement item, and discharge the specimen into the dispensing tube 11 corresponding to the measurement item. Then, the control section 4 controls the tube transfer unit 36 to set each dispensing tube 11 in which the specimen is dispensed, in the centrifuge 38 in the sample preparation section 3. Thereafter, in S24, on the basis of the information relating to preparation of measurement samples, the control section 4 controls the reagent dispenser 30B to dispense, for each measurement item, the cell detection reagents and the reagents other than the cell detection reagents into the dispensing tube 11 for preparing the measurement sample.

In the case where a plurality of cell detection reagents are mixed with the specimen in different dispensing tubes 11 to prepare measurement samples as in the second example, the control section 4, in the example shown in FIG. 13B, controls the specimen dispenser 30A to dispense the specimen into each dispensing tube 11 so that the necessary number of cells corresponding to each of the cell detection reagents 2 to 5 is attained. Next, the control section 4 controls the tube transfer unit 36 to transfer each dispensing tube 11 containing the specimen to the centrifuge 38 in the sample preparation section 3. Subsequently, the control section 4 controls the reagent dispenser 30B to dispense 5 μl of hemolyzing agent set in the reagent setting unit 35, into each dispensing tube 11 containing the specimen. The control section 4 controls the reagent dispenser 30B to dispense, in addition to the hemolyzing agent, 10 μl of a cell permeation agent set in the reagent setting unit 35 into the dispensing tube in which the cell detection reagent 5 is dispensed. Subsequently, the control section 4 controls the reagent dispenser 30B to dispense the cell detection reagents 2 to 5 set in the reagent setting unit 35 into the corresponding dispensing tubes containing the specimen. Further, the control section 4 controls the reagent dispenser 30B to dispense nucleus stain liquid (cell detection reagent 1) set in the reagent setting unit 35 into all the dispensing tubes.

Then, in S25, the control section 4 controls the tube transfer unit 36 to transfer all the dispensing tubes 11 containing the prepared measurement samples as described above, to the measurement section 2. Then, in S26, the control section 4, by using the second measurement section 2*b*, performs main measurement of the measurement samples according to the flow cytometry method.

The control section 4 may store, in the storage unit 42, the measurement item for which each measurement sample is measured, and the measurement result, in association with at least one selected from the group consisting of: the identification number (ID or the like) of the specimen; information relating to concentration information of measurement target particles; viscosity information; and the dispensing condition for the specimen. By storing the measurement result in association with the information relating to the concentration information of the measurement target particles, the viscosity information, the dispensing condition for the specimen, etc., optimization for the dispensing condition can be easily examined.

As described above, according to the sample preparing apparatus 1, the sample preparing method, and the particle analyzer 100 of the aforementioned embodiment, a specimen is subjected to pre-measurement, and concentration information of measurement target cells in the specimen is generated on the basis of data obtained through the pre-measurement. Then, preparation of a measurement sample is performed in the sample preparation section 3, with the concentration of measurement target particles in the specimen being adjusted in accordance with the generated concentration information, and cell detection reagents used for preparation of the measurement sample for main measurement. Therefore, a measurement sample that contains measurement target cells having a concentration suitable for the cell detection reagents can be efficiently prepared, whereby the measurement target cells in the specimen can be accurately analyzed.

Further, on the basis of information relating to preparation of a measurement sample, which is used for preparation of the measurement sample, operational conditions (the amount of specimen, the types of cell detection reagents necessary for preparation of the measurement sample and other reagents, the order of dispensing of the respective reagents, the dispensing amount of each reagent, etc.) for a measurement sample preparation process are controlled. Therefore, measurement sample preparation can be automatized.

Dispensing Condition and Determination of Dispensing Condition by Control Section In the embodiment of the present invention, a method of dispensing a specimen into a dispensing tube 11 can be selected from a single pipetting method and a multi pipetting method. The single pipetting method is a dispensing method in which a specimen aspirated by the nozzle 300 is discharged into the dispensing tube 11 in one time. The multi pipetting method is a dispensing method in which, when a specimen is aspirated by the nozzle 300, the specimen is aspirated by an amount that allows multiple times of discharge of the specimen, and the aspirated specimen is discharged into the dispensing tube 11 in multiple times. Preferably, in the multi pipetting method, the aspirated specimen is discharged into a plurality of dispensing tubes 11 different from each other. The single pipetting method provides excellent reproducibility of a dispensing volume. Meanwhile, when the specimen is dispensed into a plurality of dispensing tubes 11, since the nozzle 300 needs to reciprocate between the specimen container 10 and the dispensing tube 11 according to the number of times of dispensing, the dispensing takes time. The multi pipetting method is inferior in reproducibility of a dispensing volume to the single pipetting method, but can shorten the dispensing time because the number of times the nozzle 300 reciprocates between the specimen container 10 and the dispensing tube 11 is less than that in the single pipetting method. Further, in the multi pipetting method, when the specimen is stored in a specimen container (e.g., blood collection tube) with a cap (seal), multiple times of dispensing can be performed by piercing the seal one time and aspirating the specimen. Therefore, the multi pipetting method is preferable when a measurement item reluctant to contamination of the specimen is measured.

Dispensing accuracy when the specimen is dispensed, that is, whether or not the specimen can be dispensed by a volume close to a set value of a dispensing amount of the specimen, depends on the viscosity of the specimen and on a dispensing condition for aspirating and discharging the specimen by the nozzle 300. The dispensing condition includes an aspiration condition and a discharge condition for the nozzle 300.

Figure 18A:
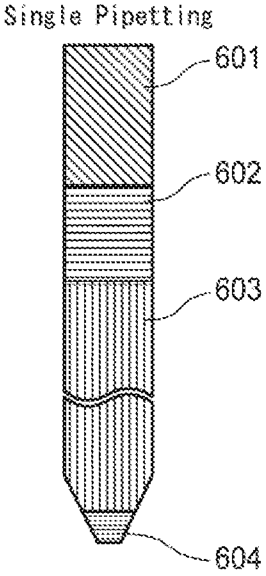
FIGS. 18A and 18B are schematic diagrams showing the inside of a nozzle that has aspirated a specimen.
Figure 18B:
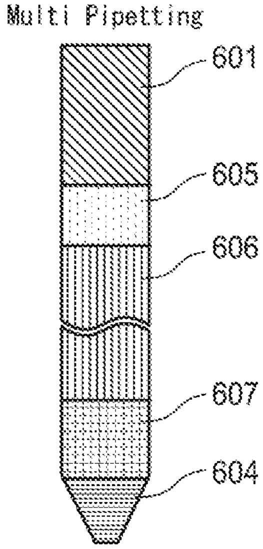

FIG. 18 is a schematic diagram showing the states inside the nozzle 300 when a specimen is aspirated, in a single pipetting method (A) and a multi pipetting method (B).

In the single pipetting method, the following are present in the nozzle 300 from the top: a system trailing airgap 601 which serves as a cylinder when a specimen is aspirated up into the nozzle 300; a leading airgap 602 for completely pushing out the specimen from the nozzle 300 when the specimen is discharged; an amount of specimen 603 necessary for one measurement; and a trailing airgap 604 for preventing liquid droplets from the nozzle 300.

In the multi pipetting method, the following are present in the nozzle 300: a system trailing airgap 601; an excess volume 605 corresponding to an excessively aspirated specimen relative to an amount of specimen necessary for performing measurement; an amount of specimen 606 necessary for multiple times of measurement; a conditioning volume 607; and a trailing airgap 604. The conditioning volume 607 is a volume for uniformizing conditions/environments between the first-time discharge and the second and subsequent times of discharges. That is, if the first-time discharge of the specimen is performed without the conditioning volume 607, this discharge is adversely affected by mechanical reaction when aspiration switches to discharge. In contrast, when the specimen aspirated as the conditioning volume 607 is discharged as "sacrifice" specimen before the first-time discharge of specimen, the mechanical reaction can be resolved. In addition, since the liquid level after the specimen aspirated as the conditioning volume 607 has been discharged comes to have a concave shape, liquid droplets are less likely to be formed, thereby providing an effect of preventing the formation of liquid droplets.

Figure 19:
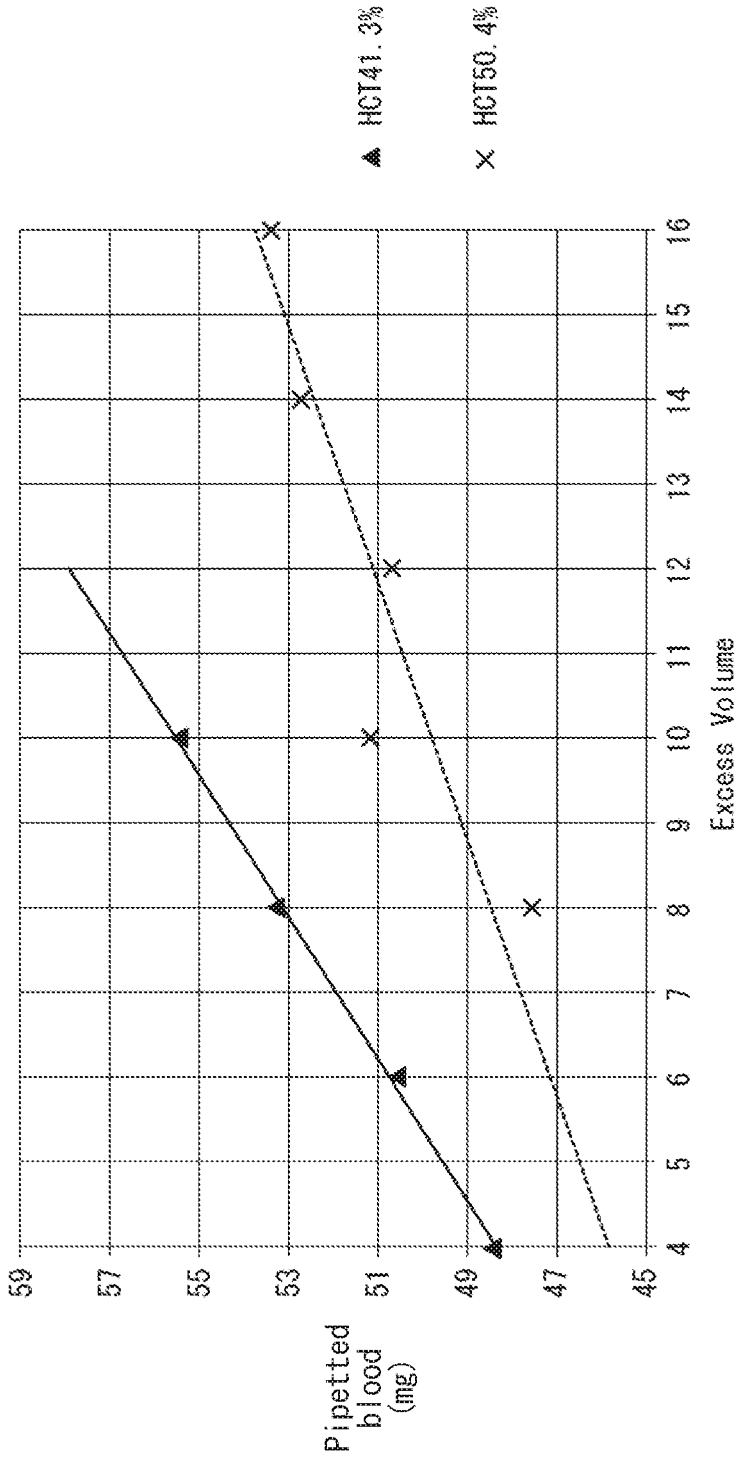
FIG. 19 is a graph showing the relationship between an excess volume and a weight of a dispensed specimen.

Aspiration conditions having influences on dispensing accuracy are, in particularly, an aspiration speed, an aspiration time, an aspiration volume (volume of specimen including an excess volume), an amount of airgap, etc. FIG. 19 shows an example of relationship between the excess volume and the weight of peripheral blood dispensed with the dispensing amount of specimen from the nozzle 300 being set to 50 μl. Theoretically, if dispensing is accurately performed, 50 μl of peripheral blood is about 53 mg in terms of weight. According to FIG. C, regarding peripheral blood having a hematocrit value of 41.3%, when the weight of the peripheral blood dispensed while changing the excess volume is measured, the weight is about 53 mg when the excess volume is 8 μl. However, with the excess volumes other than 8 the weight of the peripheral blood deviates from 53 mg. This means that dispensing closer to the set value can be performed by setting the excess volume to 8 μl. Meanwhile, regarding peripheral blood having a hematocrit value of 50.4%, a dispensing amount close to the set value cannot be attained even when the excess volume is 8 μl. For the peripheral blood having the hematocrit value of 50.4%, a dispensing amount close to the set value can be attained by increasing the excess volume to 14 μl or more. Thus, in order to perform dispensing of the specimen with a volume close to the set value of the dispensing amount, it is necessary to set, for example, the excess volume, to an appropriate volume in accordance with viscosity information of the specimen, such as a hematocrit value.

Regarding discharge conditions, in particular, discharge speed, discharge-completed speed, discharge time, discharge volume, etc. have influences on dispensing accuracy.

FIG. 20 shows examples of dispensing conditions when the single pipetting method is performed. In dispensing a specimen by using the single pipetting method, it is preferable to provide a leading airgap (LAG) 602 before aspiration of the specimen. It is possible to improve dispensing accuracy by changing the volume of the leading airgap 602 in accordance with viscosity information of the specimen. Alternatively, the aspiration speed, the aspiration time (delay), or the like may be changed to improve dispensing accuracy. In discharging the specimen, dispensing accuracy can be improved by changing, in particular, the discharge speed (dispense speed) or the discharge-completed speed (breakoff speed) in accordance with the viscosity information of the specimen. Also in the single pipetting method, an excess volume may be provided.

FIGS. 21A to 21C show examples of dispensing conditions when the multi pipetting method is performed. FIG. 21A shows dispensing conditions used in a case where the control section 4 determines in S20 that concentration adjustment for the specimen is needed because the concentration of measurement target cells in the specimen is higher than the predetermined value, determines to perform dilution of the specimen in S21, and sets the set value of the dispensing amount of the specimen to 15 μl. FIG. 21B shows dispensing conditions used in a case where the control section 4 determines in S20 that concentration adjustment of the specimen is not needed because the concentration of measurement target cells in the specimen is within the predetermined value, and sets the set value to 150 μl. FIG. 21C shows dispensing conditions used in a case where the control section 4 determines in S20 that concentration adjustment for the specimen is needed because the concentration of measurement target cells in the specimen is lower than the predetermined value, determines to perform condensation of the specimen in S21, and sets the set value to 450 μl. In the multi pipetting method, it is preferable to provide the excess volume 605. It is possible to improve dispensing accuracy by changing the excess volume 605 in accordance with the viscosity information of the specimen. Alternatively, the aspiration speed, the aspiration time (delay), or the like may be changed to improve dispensing accuracy. In discharging the specimen, dispensing accuracy can be improved by changing, in particular, the discharge speed (dispense speed) or the discharge-completed speed (breakoff speed) in accordance with the viscosity information of the specimen. Also in the multi pipetting method, the leading airgap (LAG) 602 may be provided. However, if it is difficult to provide the leading airgap 602, it is preferable to provide only the excess volume 605.

Figure 22:
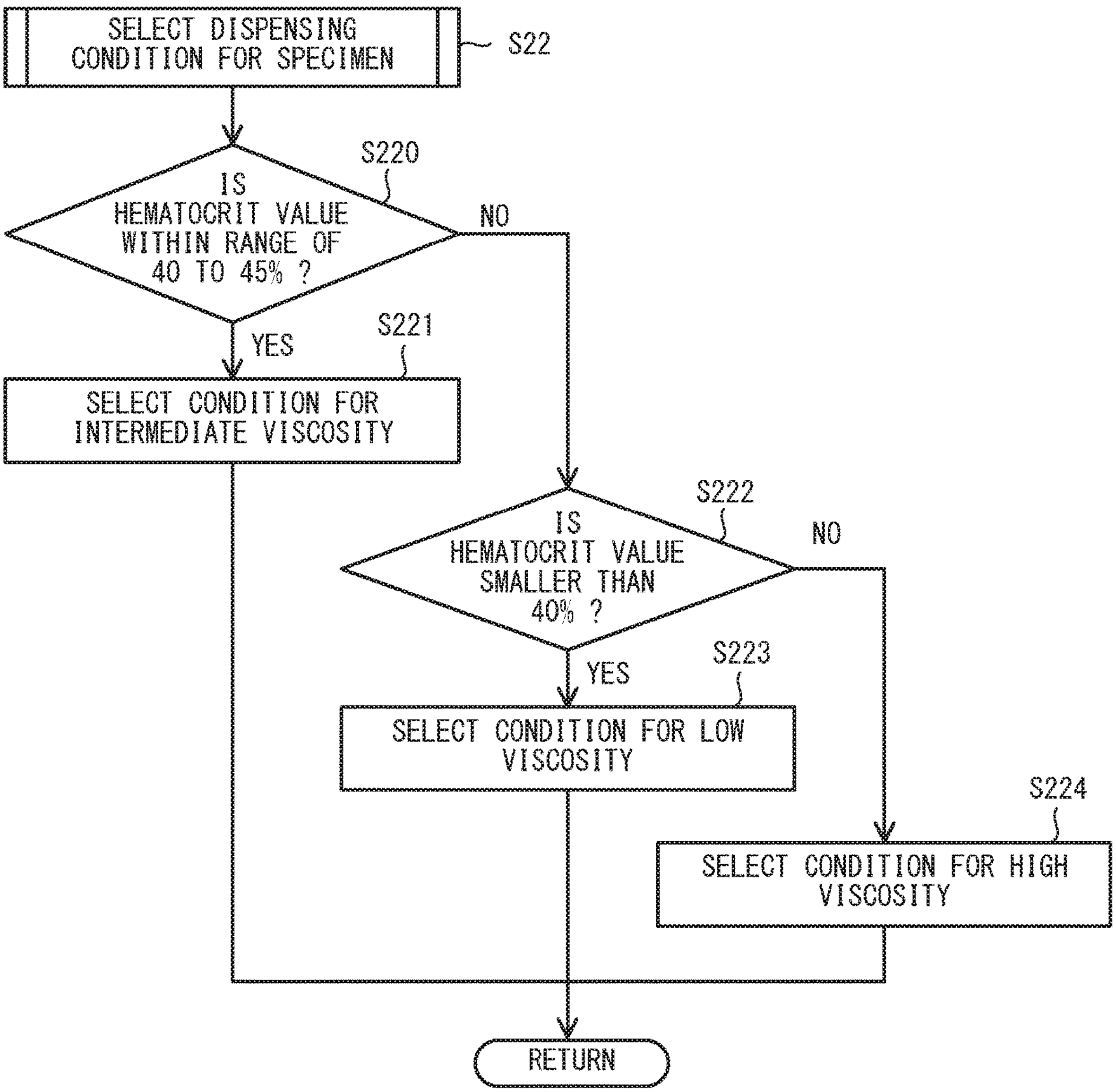
FIG. 22 is a flowchart showing an operation procedure of processing in S22 in FIG. 11.

The dispensing conditions described above are preferably stored in the storage unit 42 in advance. In S4 in FIG. 10 and in S22 in FIG. 11, the control section 4 performs the control shown in FIG. 22 to determine the dispensing conditions described above. Specifically, assuming that the viscosity information of the specimen is a hematocrit value, the control section 4 determines in S220 whether the hematocrit value obtained in S15 in FIG. 11 is within a range of 40% to 45%. When the determination result in S220 is "YES", the control section 4 proceeds to S221, and selects a condition for intermediate viscosity as a dispensing condition for the specimen. On the other hand, when the determination result in S220 is "NO", the control section 4 proceeds to S222, and determines whether or not the hematocrit value is smaller than 40%. When the determination result in S222 is "YES", the control section 4 proceeds to S223, and selects a condition for low viscosity as a dispensing condition for the specimen. When the determination result in S222 is "NO", the control section 4 proceeds to S224, and selects a condition for high viscosity as a dispensing condition for the specimen. In S23 in FIG. 11, the control section 4 causes the specimen to be dispensed into the dispensing tube 11 in accordance with the selected dispensing condition.

Change of Dispensing Condition

Figure 23:
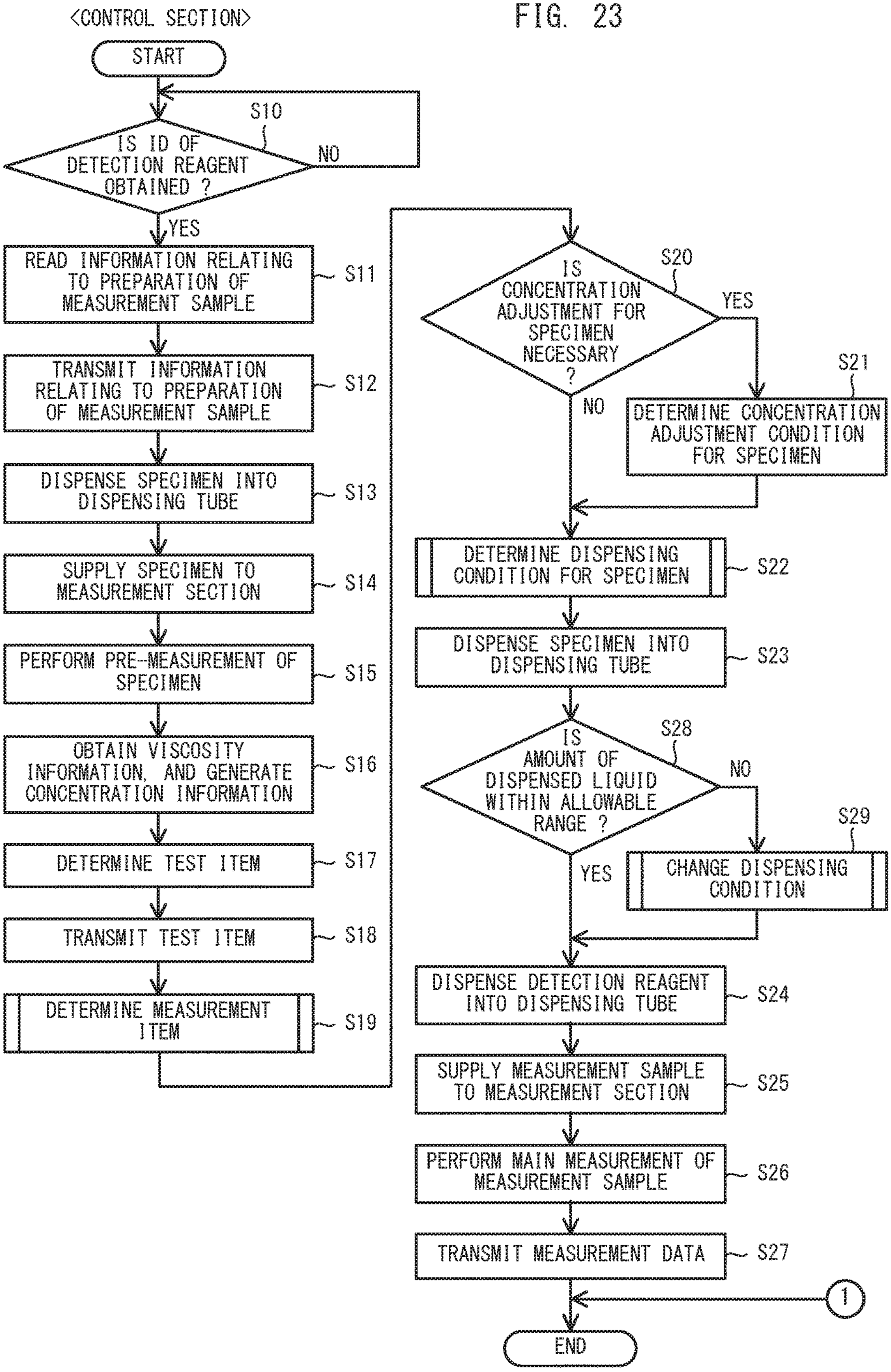
FIG. 23 is a flowchart showing an operation procedure of processing of a control section in an example where an amount of dispensed liquid is monitored.

As shown in FIG. 23, after dispensing the specimen into the dispensing tube 11 in S23 and before proceeding to S24, the control section 4 can measure the amount of the dispensed liquid for the purpose of monitoring whether or not dispensing is accurately performed. Since S10 to S23 and S24 to S27 in FIG. 23 are similar to those of the above-described embodiment, detail description thereof is omitted.

In the example shown in FIG. 23, after dispensing the specimen into the dispensing tube 11 in S23, the control section 4 controls the intra-nozzle liquid amount detecting means 30A1 or the dispensed liquid amount detecting means to detect the amount of the dispensed liquid. In S28, the control section 4 determines whether or not the liquid amount is within an allowable range in terms of dispensing accuracy. When the determination result in S28 is within the allowable range ("YES"), the control section 4 proceeds to S24.

Figure 24:
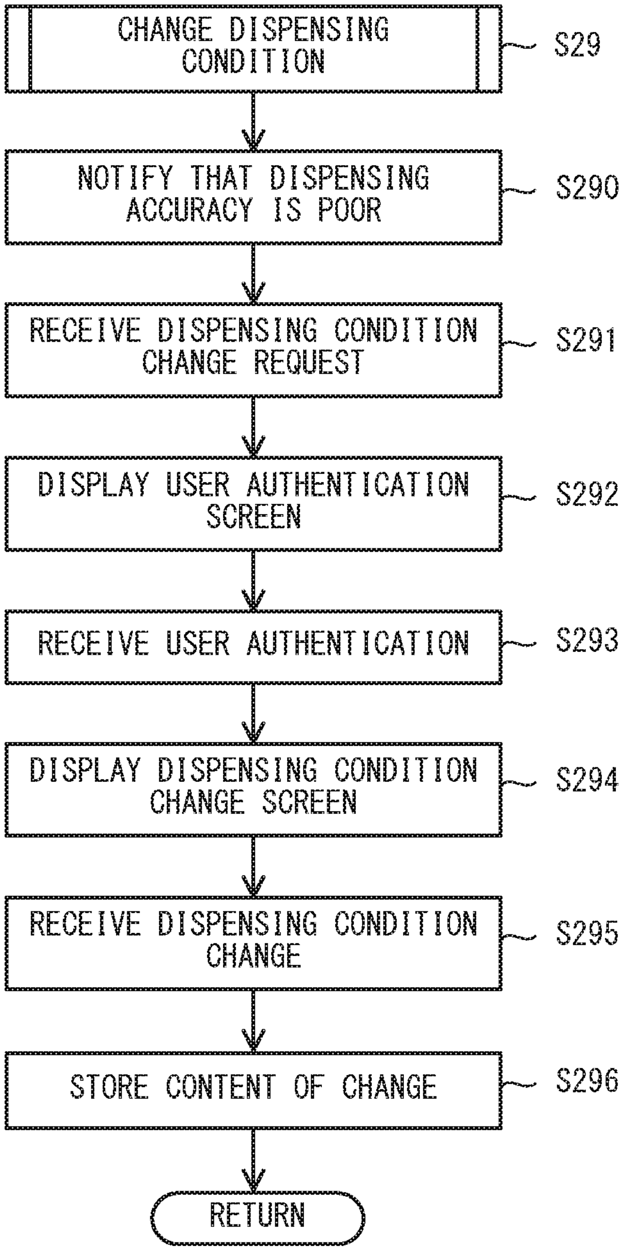
FIG. 24 is a flowchart showing an operation procedure in S29 in FIG. 23.

On the other hand, when the determination result in S28 is out of the allowable range ("NO"), the control section 4 proceeds to S29 and performs a process of changing the dispensing condition. Specifically, as shown in FIG. 24, in S290, the control section 4 notifies that dispensing accuracy is poor. This notification may be displayed on the display section 8, or may be outputted as alarm sound from the output section 10 (speaker or the like). Then, the control section 4 proceeds to S291, and receives a change of the dispensing condition, which is made by a user after the notification of poor dispensing accuracy. Such a change of the dispensing condition has influence on accuracy of the entire measurement system, and therefore, is preferably performed only by users having authority. Therefore, for example, in S291, the control section 4 receives a request to change the dispensing condition, which is inputted to the input section 9 by a user. Then, in S292, the control section 4 causes the display section 8 to display a user authentication screen for authenticating whether or not the request is made by a user having authority. Subsequently, the control section 4 proceeds to S293, and receives user authentication that is inputted to the input section 9 by the user. Upon determining that the user authentication is successful, the control section 4, in S294, causes the display section 8 to display a dispensing condition change screen (H100 in FIG. 25 and I100 in FIG. 26). Then, in S295, the control section 4 receives a change of the dispensing condition inputted to the input section 9 by the user. Then, the control section 4 proceeds to S296, and stores the content of the change in the storage unit 42. When the content of the change is stored, information including at least one selected from the group consisting of: date on which the condition has been changed; identification information (user name, user ID, or the like) of the user who has changed the condition; and the reason for the change, may be stored together with the dispensing conditions for the specimen before and after the change. By storing the content of the change of the dispensing condition, traceability can be improved.

Figure 25:
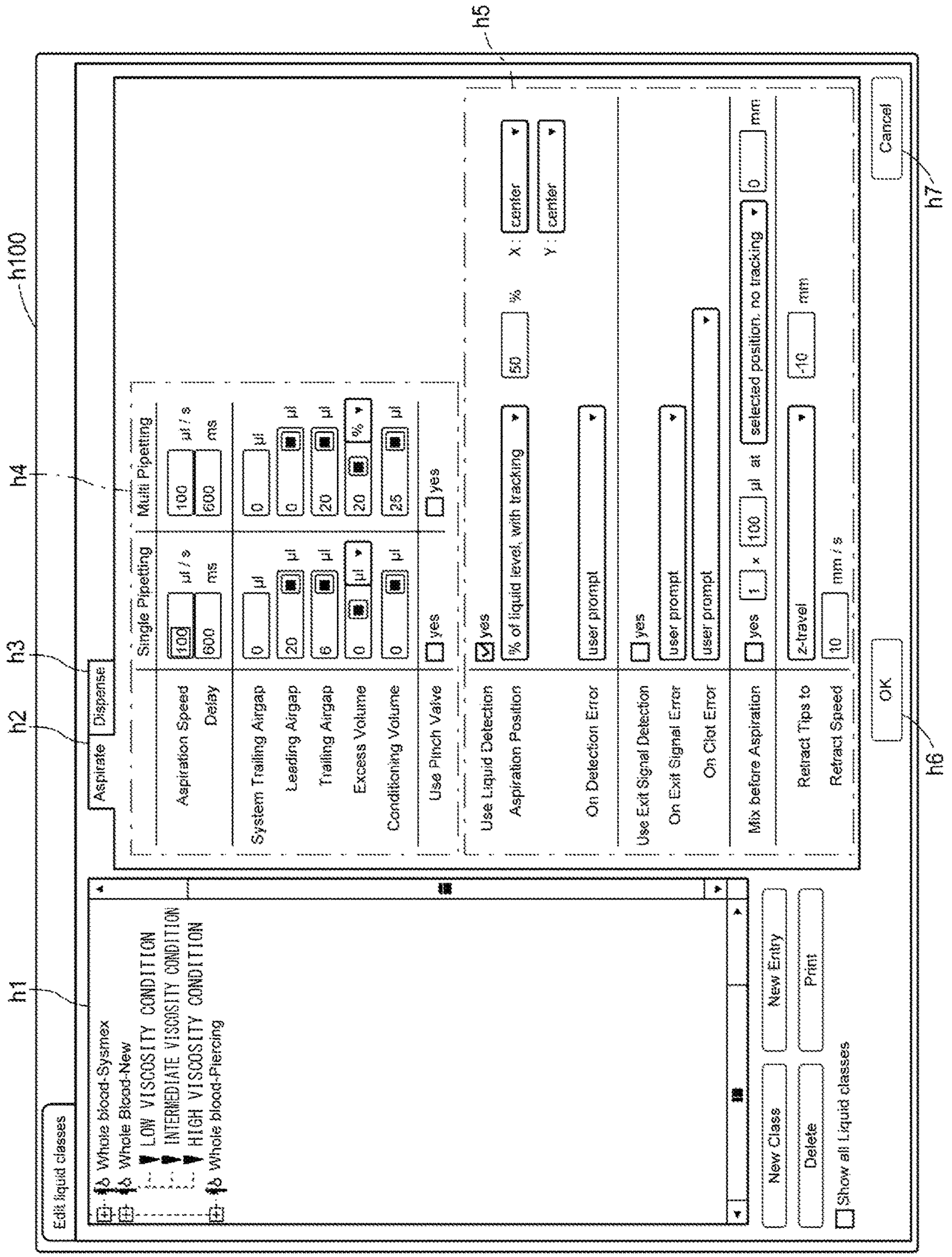
FIG. 25 shows an example of a dispensing condition change screen for changing aspiration conditions.

As shown in FIG. 25, on the dispensing condition change screen H100 for changing the aspiration condition for the nozzle 300, a viscosity condition selection area h1, an aspiration tab "Aspirate" h2 for setting aspiration conditions, and a discharge tab "Dispense" h3*tp* for setting discharge conditions, are displayed. A user performs an input operation to the input section 9 (e.g., clicks a tab with a mouse) to switch between the aspiration tab h2 and the discharge tab h3.

The aspiration tab h2 is provided with: an aspiration condition setting area h4 for setting aspiration conditions such as an aspiration speed, an aspiration time, a system trailing airgap, a leading airgap, a trailing airgap, and an excess volume, etc.; an aspiration nozzle operation setting area h5 for setting operation of the nozzle 300 during aspiration; an "OK" icon h6; and a cancel button "Cancel" h7.

Figure 26:
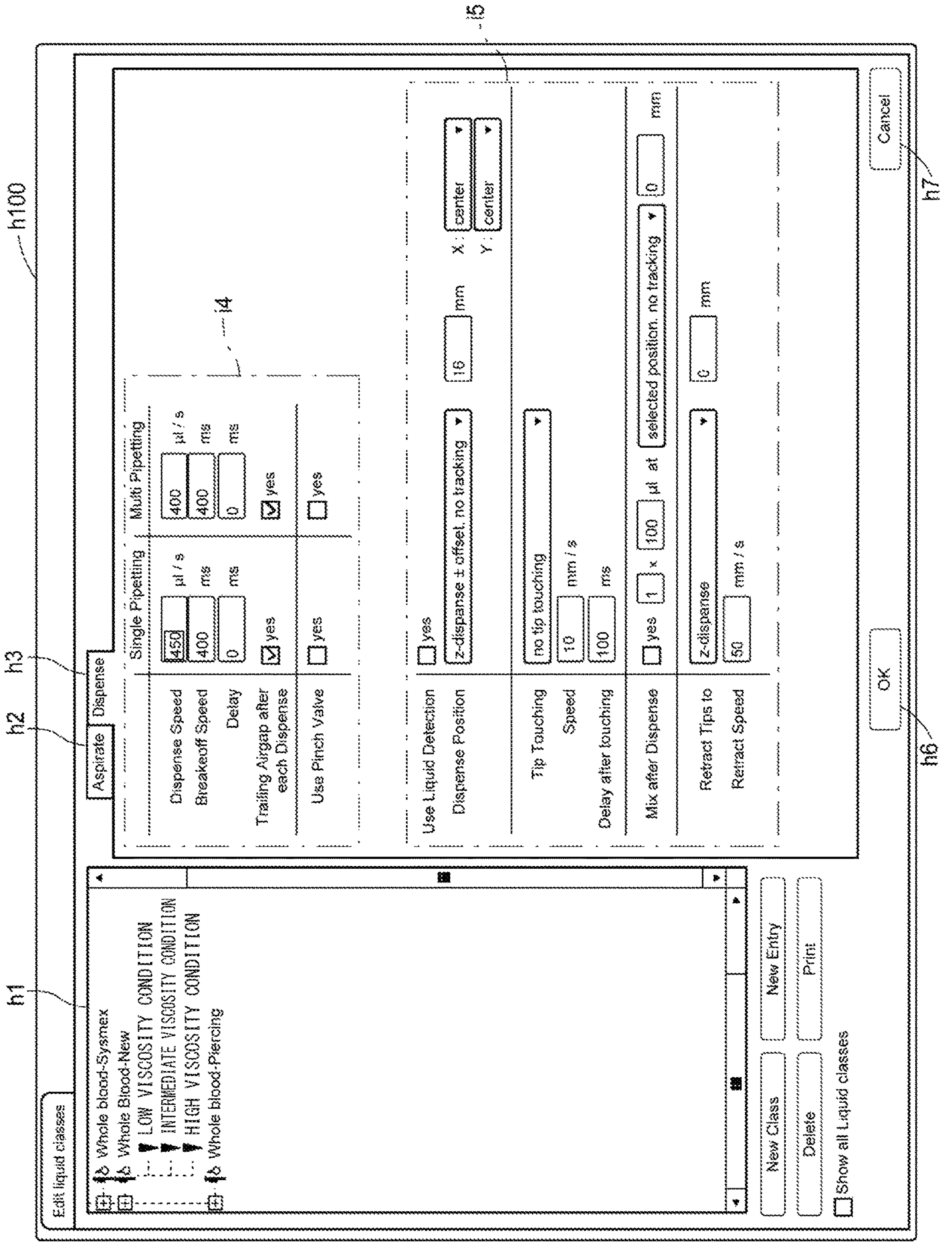
FIG. 26 shows an example of a dispensing condition change screen for changing discharge conditions.

As shown in FIG. 26, on the dispensing condition changing screen I100 for changing the discharge condition for the nozzle 300, a viscosity condition selection area h1, an aspiration tab "Aspirate" h2, and a discharge tab "Dispense" h3 are displayed. The discharge tab h3 is provided with: a discharge condition setting area i4 for setting discharge conditions such as discharge speed, breakoff speed, etc.; a discharge nozzle operation setting area i5 for setting operation of the nozzle 300 during discharge; an "OK" icon h6; and a "Cancel" button h7.

When the dispensing condition for the specimen has been changed as described above, the control section 4, in S23 in FIG. 23, dispenses the specimen into the dispensing tube 11 in accordance with the changed dispensing condition.

Other Modifications

One embodiment of a particle analyzer has been described above. However, the present invention is not limited to the above-described embodiment, and various modifications can be made without departing from the scope of the present invention.

For example, in the embodiment described above, the first measurement section 2*a* of the measurement section 2 obtains information relating to viscosity of a specimen, and the second measurement section 2*b* thereof performs detection of measurement target cells in the specimen, and main measurement of a measurement sample. However, the first measurement section 2*a* may obtain information relating to viscosity of a specimen and perform detection of measurement target cells in the specimen, and the second measurement section 2*b* may perform only main measurement of a measurement sample. In this case, a flow cytometer or the like for performing main measurement of the measurement sample can be used as the second measurement section 2*b*. The second measurement section 2*b* may be included in the sample preparing apparatus 1 or may be provided independently from the sample preparing apparatus 1. Further, electric resistance type detection means shown in FIG. A can be used as the first measurement section 2*a*. Both the electric resistance type detection means and the flow cytometry type detection means may be provided.

In the embodiment described above, the centrifuge 38 in the sample preparation section 3 functions as a concentration adjustment unit. However, the specific configuration for concentration adjustment is not particularly limited, and a filter, a cell sorter, or the like may be used.

In the embodiment described above, the sample preparation section 3 includes the centrifuge 38, and preparation of a measurement sample is performed by the centrifuge 38. However, the specific configuration for preparing a measurement sample is not particularly limited, and any configuration may be used as long as it can automatically prepare a measurement sample.

In the embodiment described above, the reception unit 39 provided in the reagent setting unit 35 in the reagent preparation section 3 determines a test item and measurement items for a specimen, on the basis of information relating to cell detection reagents set in the reagent setting unit 35. However, a barcode, a tag, or the like in which information for specifying a measurement item is stored may be attached to each specimen container 10, and the specimen container setting unit 31 may be provided with a reception part such as a barcode reader, an RFID reader, or the like capable of reading the barcode or the like. The reception part may read the barcode or the like attached to the specimen container 10 to obtain the information for specifying the measurement item. Information for specifying a measurement item is not limited as long as it allows the measurement item to be specified. For example, name of a measurement item, or identification information or name of a reagent necessary for measuring a measurement item may be used.

In the embodiment described above, the control section 4 may determine the number of measurement samples to be prepared by the sample preparation section 3, on the basis of the types of particle detection reagents used for preparation of measurement samples, and the number of measurement target particles in a specimen contained in each specimen container. For example, information relating to the number of measurement samples (dispensing tubes 11) necessary for measurement may be included in information relating to preparation of measurement samples. When preparing measurement samples, the control section 4 may control the sample preparation section 3 so as to prepare a predetermined number of measurement samples, on the basis of the number of measurement target cells in the specimen contained in each specimen container 10, and the information relating to the number of measurement samples (dispensing tubes 11) necessary for measurement, which is included in the information relating to preparation of measurement samples.

Figure 16:
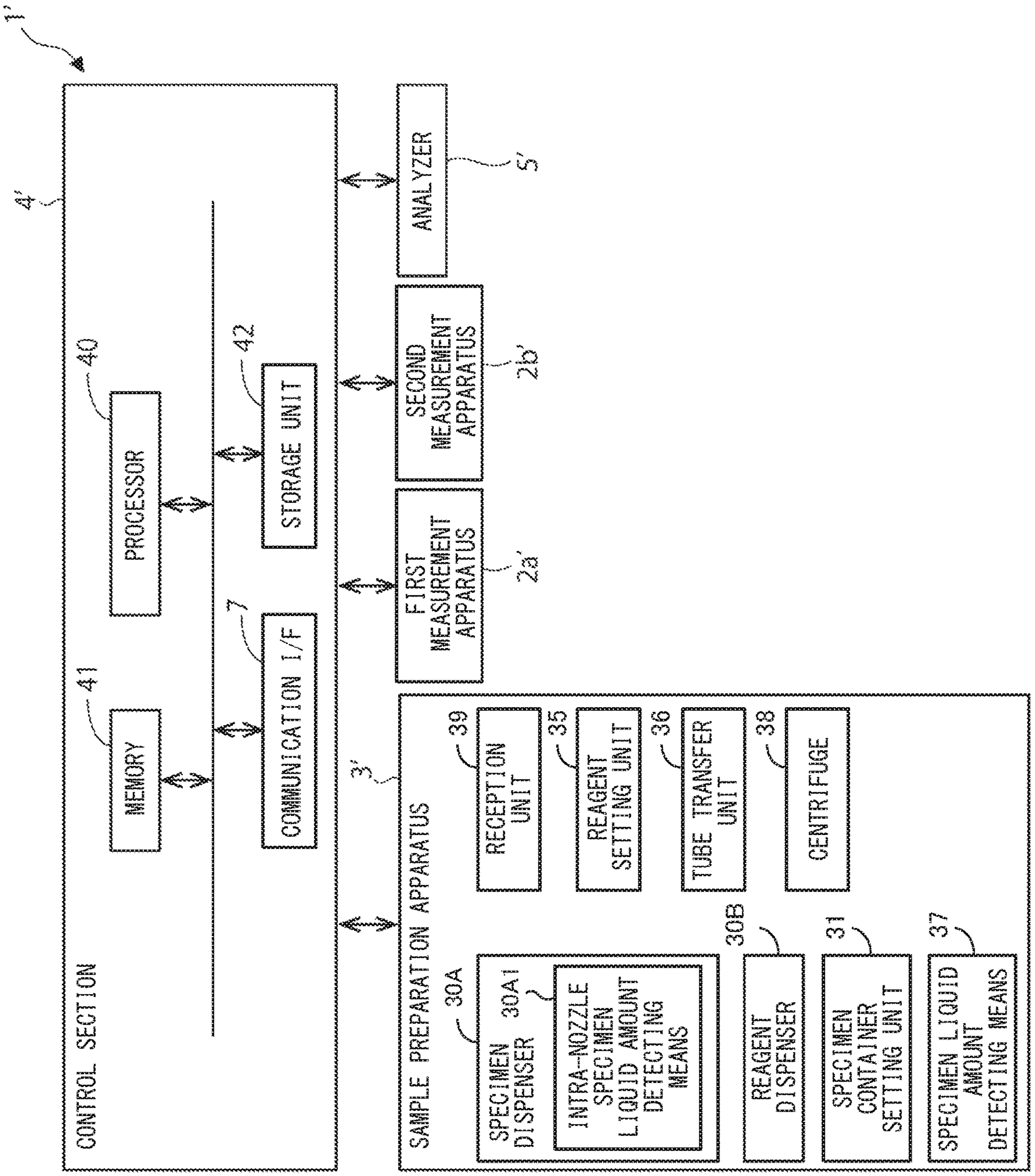
FIG. 16 is a block diagram of a sample preparing system.

In the embodiment described above, the sample preparing apparatus 1 is configured as a single apparatus that integrally includes the measurement section 2 (the first measurement section 2*a* and the second measurement section 2*b*), the sample preparation section 3, and the control section 4. However, the present invention is not limited to the above-described embodiment, and may be a sample preparing system 1' in which, as shown in FIG. 16, the first measurement section 2*a*, the second measurement section 2*b*, the sample preparation section 3, and the control section 4 are configured as independent apparatuses, i.e., a first measurement apparatus 2*a*', a second measurement apparatus 2*b*', a sample preparing apparatus 3', and a control device 4', respectively, and the first measurement apparatus 2*a*', the second measurement apparatus 2*b*', the sample preparing apparatus 3', and an analyzer 5' are connected to the control device 4. The first measurement apparatus 2*a*', the second measurement apparatus 2*b*', the sample preparing apparatus 3', the control device 4', and the analyzer 4' have the same or substantially same structures as the first measurement section 2*a*, the second measurement section 2*b*, the sample preparation section 3, the control section 4, and the analysis section 5 shown in FIG. 1, respectively. In this case, the signal processing section 6 shown in FIG. 1 is included in each of the first measurement apparatus 2*a*' and the second measurement apparatus 2*b*', and a communication I/F is included in each of the apparatuses 2*a*', 2*b*', and 3' to 5'.

What is claimed is:

1. A sample preparing apparatus comprising:
   - a sample preparation section comprising a specimen dispenser configured to aspirate a specimen from a specimen container and discharge the aspirated specimen into a mixing container to be mixed with a reagent in the mixing container to prepare a measurement sample;
   - a measurement section comprising:
   - a first measurement section further comprising an electric resistance detector and is configured to obtain viscosity information calculated based on electric characteristics measured by the electric resistance detector relating to the viscosity of the specimen;

a second measurement section further comprising a flow cytometer and is configured to measure cells in the specimen; and a control section connected to the sample preparation section and the measurement section and programmed to control the specimen dispenser to aspirate or discharge the specimen in accordance with a condition based on the viscosity information.

2. The sample preparing apparatus of claim 1, wherein the control section is further programmed to control the specimen dispenser to discharge the aspirated specimen into the mixing container to be mixed with the reagent that includes a labeling substance.

3. The sample preparing apparatus of claim 1, wherein the control section is further programmed to:

determine a dispensing condition so that an amount of the specimen according to a concentration of measurement target particles is discharged into the mixing container.

4. The sample preparing apparatus of claim 1, wherein the control section is further programmed to control the specimen dispenser to aspirate or discharge the specimen based on the viscosity information that includes at least one of a hematocrit value of the specimen, the number of red blood cells per unit volume, the number of white blood cells per unit volume, the number of platelets per unit volume, or a mean corpuscular volume value.

5. The sample preparing apparatus of claim 1, wherein the control section is further programmed to:

control the specimen dispenser to aspirate the specimen from the specimen container; and control the specimen dispenser to aspirate the specimen based on an aspiration condition that includes at least one of an aspiration speed, an aspiration time, an aspiration volume, or an amount of airgap.

6. The sample preparing apparatus of claim 1, wherein the control section is further programmed to:

control the specimen dispenser to discharge the specimen into the mixing container; and control the specimen dispenser to discharge the specimen based on a discharge condition that includes at least one of a discharge speed, a discharge time, or a discharge volume.

7. The sample preparing apparatus of claim 1, wherein the control section is further programmed to control the specimen dispenser to discharge the aspirated specimen, in one time or in a plurality of times.

8. The sample preparing apparatus of claim 1, wherein the sample preparation section further includes a liquid amount detecting unit configured to detect a liquid amount of the specimen discharged for preparing the measurement sample.

9. The sample preparing apparatus of claim 8, wherein the liquid amount detection unit is further configured to:

detect of the liquid amount of the specimen based on a liquid level of the discharged specimen and a weight of the discharged specimen.

10. The sample preparing apparatus of claim 8, wherein the liquid amount detection unit is further configured to:

when the aspirated specimen is discharged a plurality of times, detect a liquid level of the aspirated specimen before and after each discharge.

11. The sample preparing apparatus of claim 1, the control section is further programmed to:

control an operation of an input section and a display section, wherein the input section and the display section are operatively connected to the control section; and cause the display section to display a dispensing condition change screen, when receiving a dispensing condition change request from the input section.

12. The sample preparing apparatus of claim 11, wherein the control section is further programmed to:

cause the display section to display a user authentication screen;

receive a request for user authentication from the input section; and cause the display section to display the dispensing condition change screen when a user who has performed the authentication has predetermined authority.

13. The sample preparing apparatus of claim 12, wherein the control section is further programmed to:

when the dispensing condition for the specimen has been changed, store in a storage unit at least one of dispensing conditions for the specimen before and after the change, date on which the condition has been changed, identification information of a user who has changed the condition, or a reason for the change, wherein the storage unit is operatively connected to the control section.

14. The sample preparing apparatus of claim 13, wherein the control section is further programmed to:

store in the storage unit a measurement item for which the measurement sample is measured, and a result of measurement, in association with at least one of information relating to concentration information of measurement target particles, viscosity information, or a dispensing condition for the specimen.

15. The sample preparing apparatus of claim 2, wherein the sample preparation section further comprises:

a reagent dispenser configured to dispense a plurality of types of labeling substances into the mixing container to prepare the measurement sample, wherein the reagent dispenser is included in the specimen dispenser.

16. The sample preparing apparatus of claim 1, wherein the second measurement section further comprises:

a flow cell;

a light source configured to apply light to the specimen passing through the flow cell; and a light receiving element configured to detect optical information from a particle in the specimen and convert the optical information into an electric signal.

17. The sample preparing apparatus according to claim 1, wherein the sample preparation section is further configured to:

prepare a measurement sample from at least a first portion of the specimen in the specimen container after a second portion of the specimen in the specimen container is measured.

18. A sample preparing system comprising:

a sample preparing apparatus comprising a specimen dispenser configured to aspirate a specimen from a specimen container and discharge the aspirated specimen into a mixing container to be mixed with a reagent in the mixing container to prepare a measurement sample;

a measurement apparatus comprising:

a first measurement apparatus further comprising an electric resistance detector and is configured to obtain viscosity information calculated based on electric characteristics measured by the electric resistance detector relating to the viscosity of the specimen; and a second measurement apparatus further comprising a flow cytometer and is configured to measure cells in the specimen; and a control device connected to the sample preparing apparatus and the measurement apparatus, the control device programmed to:

receive, from the first measurement apparatus, the viscosity information via a communication interface included in the control section; and control the specimen dispenser to aspirate or discharge the specimen in accordance with a condition based on viscosity information obtained from the first measurement apparatus.

19. A particle analyzer comprising:

a sample preparation section comprising a specimen dispenser configured to aspirate a specimen from a specimen container and discharge the aspirated specimen into a mixing container to be mixed with a reagent in the mixing container to prepare a measurement sample;

a control section connected to the sample preparation section and a measurement section and programmed to control the specimen dispenser to dispense the specimen into the mixing container in accordance with a dispensing condition based on a viscosity of the specimen;

the measurement section comprising:

a first measurement section further comprising an electric resistance detector and is configured to obtain viscosity information calculated based on electric characteristics measured by the electric resistance detector relating to the viscosity of the specimen;

a second measurement section further comprising a flow cytometer and is configured to:

measure cells in the specimen; and measure the measurement sample prepared by the sample preparation section to detect measurement target particles in the measurement sample; and an analysis section configured to analyze the measurement target particles based on measurement data obtained by the second measurement section.

20. The sample preparing system of claim 18, wherein the sample preparation apparatus is further configured to mix the specimen with the reagent that includes a labeling substance.

21. The sample preparing system of claim 18, wherein the control device is further programmed to control the specimen dispenser to discharge the aspirated specimen in one time or in a plurality of times.

22. The sample preparing system of claim 18, wherein the sample preparing apparatus further comprises:

a reagent dispenser configured to dispense a plurality of types of labeling substances into the mixing container to prepare the measurement sample, wherein the reagent dispenser is included in the specimen dispenser.

* * * * *